United States Patent
Krause et al.

(10) Patent No.: US 12,162,918 B2
(45) Date of Patent: Dec. 10, 2024

(54) PERIOSTIN COMPOUNDS FOR THE TREATMENT OF HAEMATOLOGICAL COMPLICATIONS

(71) Applicant: Chemotherapeutisches Forschungsinstitut Georg-Speyer-Haus, Frankfurt am Main (DE)

(72) Inventors: Daniela S. Krause, Frankfurt am Main (DE); Divij Verma, New York, NY (US)

(73) Assignee: CHEMOTHERAPEUTISCHES FORSCHUNGSINSTITUT GEORG-SPEYER-HAUS, Frankfurt am Main (DE)

( * ) Notice: Subject to any disclaimer, the term of this patent is extended or adjusted under 35 U.S.C. 154(b) by 739 days.

(21) Appl. No.: 17/260,681

(22) PCT Filed: Jul. 18, 2019

(86) PCT No.: PCT/EP2019/069345
§ 371 (c)(1),
(2) Date: Jan. 15, 2021

(87) PCT Pub. No.: WO2020/016346
PCT Pub. Date: Jan. 23, 2020

(65) Prior Publication Data
US 2021/0261638 A1    Aug. 26, 2021

Related U.S. Application Data

(60) Provisional application No. 62/700,465, filed on Jul. 19, 2018.

(30) Foreign Application Priority Data

Jul. 19, 2018 (EP) .................................. 18184430

(51) Int. Cl.
| | |
|---|---|
| C07K 14/51 | (2006.01) |
| A61K 35/28 | (2015.01) |
| A61K 38/00 | (2006.01) |
| C12N 5/0789 | (2010.01) |

(52) U.S. Cl.
CPC .............. C07K 14/51 (2013.01); A61K 35/28 (2013.01); C12N 5/0647 (2013.01); A61K 38/00 (2013.01); C12N 2501/155 (2013.01)

(58) Field of Classification Search
None
See application file for complete search history.

(56) References Cited

U.S. PATENT DOCUMENTS

| | | |
|---|---|---|
| 2010/0166827 A1 | 7/2010 | Kuhn |
| 2011/0033516 A1 | 2/2011 | Markwald et al. |
| 2012/0071407 A1* | 3/2012 | Hamilton ................ A61P 17/02 514/44 R |
| 2013/0216507 A1 | 8/2013 | Zon et al. |
| 2014/0051630 A1 | 2/2014 | Rudnicki et al. |
| 2021/0261638 A1* | 8/2021 | Krause ..................... A61P 7/00 |

OTHER PUBLICATIONS

International Search Report and Written Opinion, International Patent Application No. PCT/EP2019/069345, Oct. 4, 2019 (14 pages).
Verma, Divij et al., "Impairment of the bone marrowmicroenvironment and hematopoiesis by warfarin", Experimental Hematology, vol. 53, Jan. 1, 2017 (1 page).
Tanaka, Satowa et al., "Periostin supports hematopoietic progenitor cells and niche-dependent myeloblastoma cellsin vitro", Biochemical and Biophysical Research Communications, Elsevier, vol. 478, No. 4, pp. 1706-1712, Sep. 3, 2016.

* cited by examiner

Primary Examiner — Blaine Lankford
(74) Attorney, Agent, or Firm — Merchant & Gould P.C.

(57) ABSTRACT

The present invention pertains to periostin compounds for use in the prevention and treatment of haematological complications, such as adverse events from therapy or haematological diseases. In context of the present invention a therapeutic was developed for enhancing haematopoiesis in patients and to support haematopoietic stem cell (HSC) transplantation (HSCT) by administration of periostin compounds to patients or stem cell donors, or by contacting HSC directly with periostin compounds, for example ex vivo, to improve a transplant HSC preparation. The present invention provides periostin derived compounds such as polypeptides, peptides, nucleic acids, and other periostin-derived agents, that are used both in therapeutic applications and for improving haematopoiesis, for example in stem cell donor subjects or to treat HSC in vitro.

Figure 1:
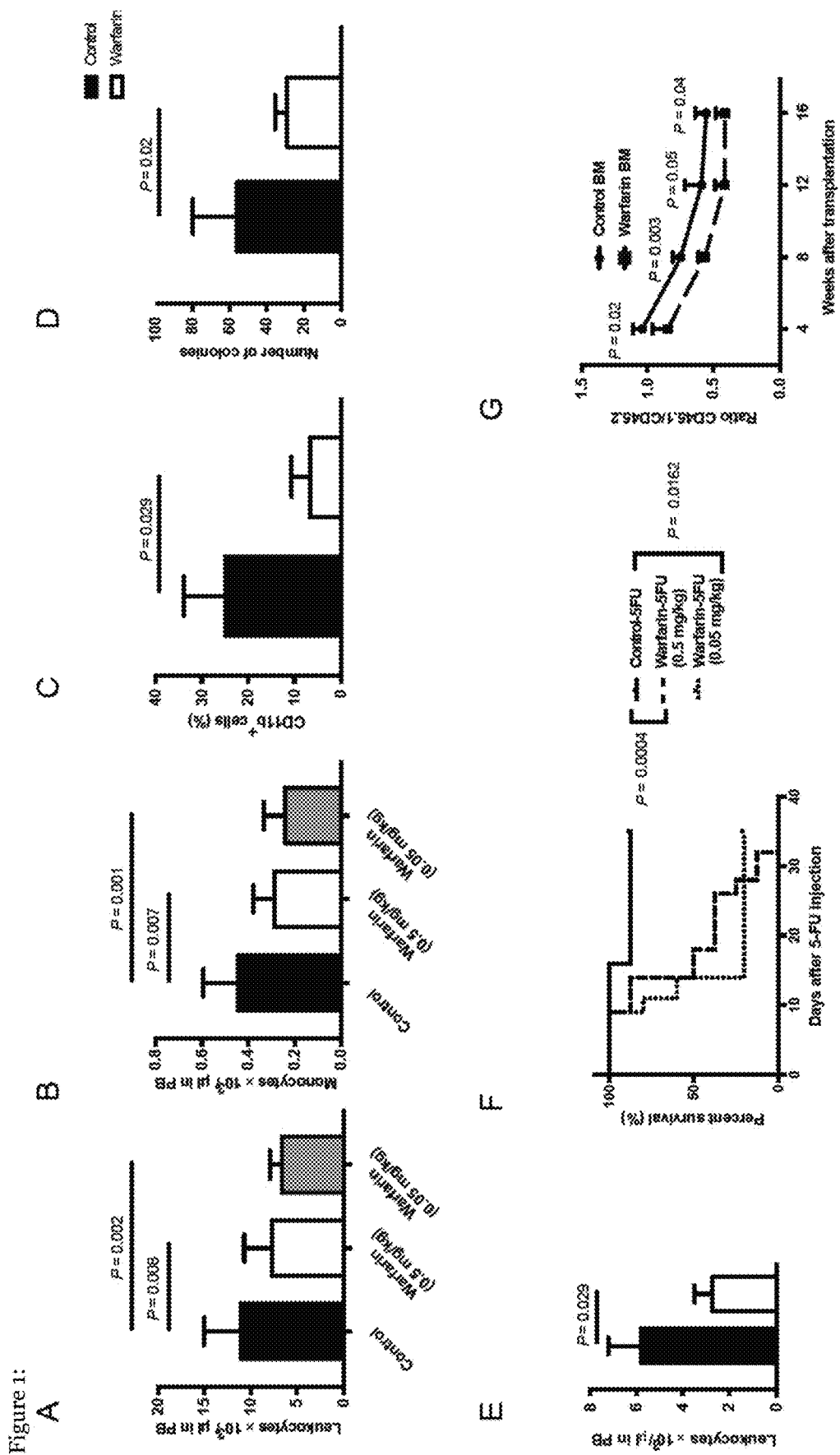
Figure 1:
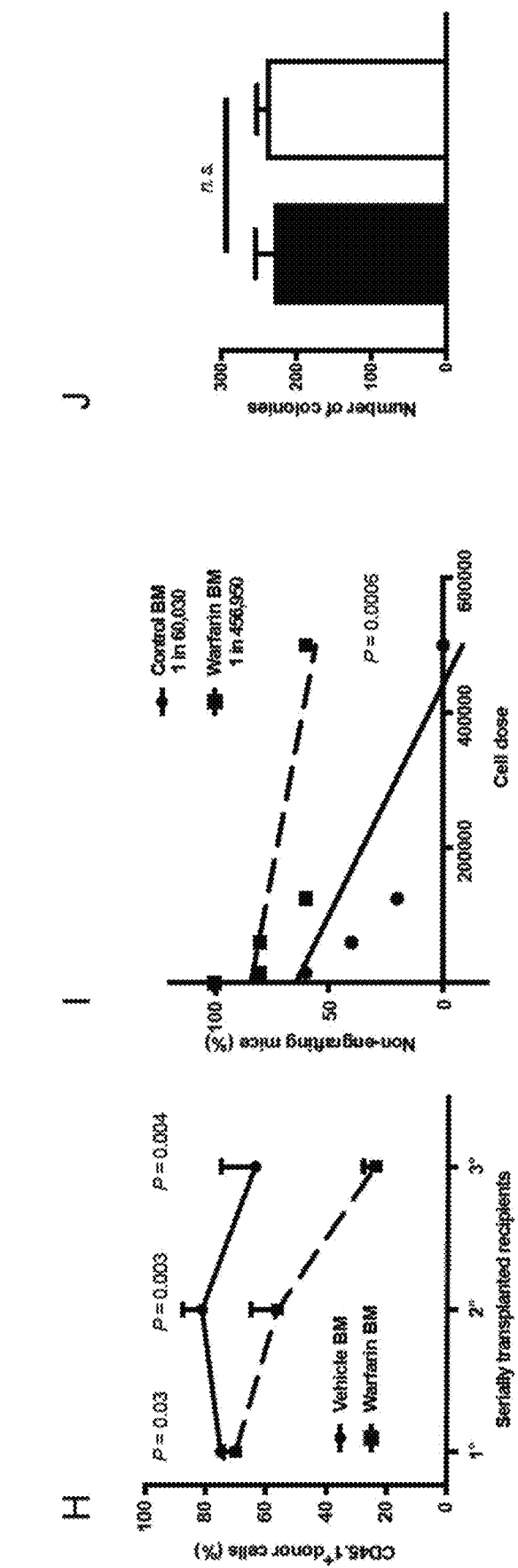

4 Claims, 12 Drawing Sheets
Specification includes a Sequence Listing.

PERIOSTIN COMPOUNDS FOR THE TREATMENT OF HAEMATOLOGICAL COMPLICATIONS

FIELD OF THE INVENTION

The present invention pertains to periostin compounds for use in the prevention and treatment of haematological complications, such as adverse events from therapy or haematological diseases. In context of the present invention a therapeutic strategy was developed for enhancing haematopoiesis in patients and to support haematopoietic stem cell (HSC) transplantation (HSCT) by administration of periostin compounds to patients or stem cell donors, or by contacting HSC directly with periostin compounds, for example ex vivo, to improve a transplant of HSC. The present invention provides periostin derived compounds such as polypeptides, peptides, nucleic acids, and other periostin-derived agents, that are used both in therapeutic applications and for improving haematopoiesis, for example in stem cell donor subjects or to treat HSC in vitro.

DESCRIPTION

Hematopoiesis is the dynamic and continuous process of the production of blood cells from HSC. HSC reside in the bone marrow cavity along with various other bone marrow niche cells such as mesenchymal stem cells (MSC), osteoblastic cells, adipocytes, chondrocytes, endothelial cells, macrophages etc. Various components of this BMM, including extracellular matrix proteins, regulate different HSC functions such as self-renewal capacity, differentiation potential, mobilization etc., either via secreting HSC supportive cytokines or via directly binding to HSC.

Stress conditions such as infection, chemotherapy (for the treatment of blood or solid cancers), blood loss etc. increase the differentiation of HSC and their progenitors, ideally leading to the eradication of infectious particles or the compensation of the loss of blood cells and platelets. Repetitive or continuous haematopoietic stress has been shown to be linked to HSC exhaustion and a reduction of HSC number and/or function, for instance after repeated chemotherapy. HSC exhaustion and a reduction of HSC function have also been linked with impaired hematopoiesis in elderly patients (Periostin and haematopoiesis D. Verma, D. S. Krause) Ich verstehen diesen vorherigen Satz nicht. Sollte es heissen: (Periostin and haematopoiesis D. Verma, D. S. Krause)?. In addition, ageing has been associated with recurrent somatic mutations in HSC that have been detected in more than 10% of people older than 65 years. Impaired haematopoiesis may lead to certain health issues such as frequent infection or bleeding, and recurrent somatic mutations can give rise to haematological malignancies such as myelodysplastic syndrome (MDS) and others.

I. Haematopoietic stem cell transplantation (HSCT) for various haematological diseases is a potentially life-threatening procedure associated with severe adverse events and problems. Problems associated with HSCT are a) engraftment failure, for instance in heavily pre-treated patients, or b) the relative lack of matched donor HSC.

II. The other clinical scenario in which augmentation of haematopoiesis is desired are MDS and bone marrow failure syndromes such as aplastic anaemia. Patients with these conditions are treated by the administration of growth factors, transfusions or HSCT, as described above. However, these treatments are frequently not sufficient to stimulate or support haematopoiesis and other treatments are needed.

Several haematological problems or diseases such as inefficient engraftment of donor HSC after transplantation, MDS or bone marrow failure syndromes prevent a patient from appropriately reacting to haematopoietic stress. This renders a patient vulnerable to the effects of anaemia, infection or bleeding. Shortening the times of these vulnerabilities or preventing them altogether is a daily goal in clinical haematology. Novel drugs are needed to augment deficient haematopoiesis, either alone or in combination with the transfusion of blood products.

It is an object of the present invention to develop a new therapeutic tool to enhance haematopoiesis in order to improve HSCT treatment success, and to counter adverse events associated with drugs that impair normal haematopoiesis in patients.

The problem is solved in a first aspect by a periostin compound for use in the prevention or treatment of a haematological disorder in a subject, wherein the periostin compound is selected from a periostin protein, or a functional fragment or variant thereof, or a periostin nucleic acid encoding the periostin protein, or encoding the functional fragment or variant thereof.

Periostin is a high molecular weight protein secreted by mesenchymal stem cells and osteoblastic cells in the bone marrow niche or microenvironment (BMM). It binds to alpha-V/beta-3 and alpha-V/beta-5 integrins and was recently shown to influence haematopoietic stem cell (HSC) function via binding to integrin-av (Itgav). The term "periostin protein" also known as "osteoblast factor 2" or "OSF-2" is used herein to encompass mammalian and non-mammalian periostin proteins, including human and non-human (mammalian) periostin, and functionally equivalent forms thereof. Human periostin (e.g. the wildtype isoform) is an 836 amino acid protein, and examples of functionally equivalent forms thereof include, for example, human isoforms 2, 3 and 4. SEQ ID Nos 1 to 7 represent all 7 human periostin variants.

A periostin protein in accordance with the invention is a protein comprising an amino acid sequence that is at least 50%, more preferably 60, 70, 80, 90, 95, 96, 97 and most preferably 98% identical to any one of amino acid sequences shown in SEQ ID NOs: 1 to 7. Even more preferred is a periostin protein having 99% or 100% sequence identity to any one of the amino acid sequences shown in SEQ ID NOs: 1 to 7.

The term "variant" as referred to herein, means a polypeptide substantially identical to the original or reference amino acid sequence, but which has at least one amino acid sequence different from that of the original sequence because of one or more deletions, insertions or substitutions. Therefore, as used herein, the terms "identical" or percent "identity", when used anywhere herein in the context of two or more nucleic acid or protein/polypeptide sequences, refer to two or more sequences or sub-sequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region-preferably over their full length sequences-, when compared and aligned for maximum correspondence over the comparison window or designated region) as measured using a sequence comparison algorithms, or by manual alignment and visual inspection (see, e.g., NCBI web site). In a particular embodiment, the percentage identity can be determined by the Blast searches for amino acid identity, those using BLASTP 2.2.28+ with the following parameters: Matrix: BLOSUM62; Gap Penalties: Existence: 11, Extension: 1; Neighboring words threshold: 11; Window for multiple hits: 40.

A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as He, Val, Leu, or Ala for one another, or substitutions of one polar residue for another, such as between Lys and Arg; Glu and Asp; or Gin and Asn. Other such conservative substitutions, for example, substitutions of entire regions having similar hydrophobicity characteristics, are well known (Kyte, et al, 1982, J. Mol. Biol, 157:105-131). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired.

A periostin compound in accordance with the herein disclosed invention may be obtained from any means known to the skilled artisan. In particular preferred periostin compounds are recombinantly expressed and then optionally isolated and purified before use. The term "recombinant expression" in context of the herein disclosed invention shall refer to the expression of a protein or peptide by introduction of an exogenous expression vector transiently or stably into a host cell and the following expression of the protein from the vector in the host cell. Typically, recombinant expression is achieved by the introduction of a recombinant expression vector into the host cell of choice. Such recombinant expression vectors are provided by the invention and comprise a nucleic acid molecule encoding a periostin compound which is a protein or peptide, and wherein the vector optionally comprises an expression control sequence, allowing expression in prokaryotic or eukaryotic host cells of the encoded polypeptide, operably linked to said nucleic acid molecule.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses. These recombinant vectors can equally be cosmid or phagemid derivatives.

The nucleic acid sequence can be inserted in the recombinant expression vector by methods well known to a person skilled in the art such as, for example, those that are described in MOLECULAR CLONING: A LABORATORY MANUAL, Sambwok et al, 4th Ed., Cold Spring Harbor Laboratory Press, Cold Spring Harbor, N.Y., 2001.

The recombinant vector can include nucleotide sequences that allow, control or regulate the expression and the transcription of a polynucleotide of the invention as well as the translation of a polypeptide of the invention, these sequences being selected according to the host cells that are used.

Thus, for example, an appropriate secretion signal can be integrated in the recombinant vector so that the polypeptide, encoded by the nucleic acid molecule of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al, 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *E. coli* or *Streptomyces*, cells of fungi such as *Aspergillus* and yeasts such as *Saccharomyces*, insect cells, Chinese Hamster Ovary cells (CHO), CI 27 mouse cell line, BHK cell line of Syrian hamster cells, Human Embryonic Kidney 293 (HEK 293) cells. In a particular embodiment, the host cell is a CHO cell or a HEK 293 cell.

The host cells can be used, for example, to express a periostin compound of the invention. After purification by standard methods, the periostin compound of the invention can be used in a method or application described herein elsewhere.

For instance, when expression systems that secrete the recombinant protein are employed, the culture medium may first be concentrated using a commercially available protein concentration filter, for example, an Amicon or Millipore Pellicon ultrafiltration unit. Following the concentration step, the concentrate can be applied to a purification matrix such as a gel filtration matrix. Alternatively, an anion exchange and/or an affinity resin can be employed. The matrices can be acrylamide, agarose, dextran, cellulose or other types commonly employed in protein purification. Alternatively, a cation exchange step can be employed. Finally, one or more reversed-phase high performance liquid chromatography (RP-HPLC) steps employing hydrophobic RP-HPLC media can be employed to further purify the antibodies or fragments thereof. Some or all of the foregoing purification steps, in various combinations, are well known and can be employed to provide a substantially homogeneous recombinant protein.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of cell lysing agents.

In another embodiment, the invention provides a process for producing cells capable of expressing a polypeptide according to the invention, comprising genetically engineering cells with a vector or a nucleic acid according to the invention.

In one additional embodiment the invention also includes the use of a periostin compound that is directly isolated and optionally purified from a biological sample comprising such periostin compounds. Periostin may be purified from human plasma from healthy blood or plasma donors by various precipitation steps. Such isolation and purification methods of proteins from biological samples such as blood or plasma samples are well known to the skilled artisan.

In context of the present invention the periostin compounds are used in medical applications and preferably for the prevention or treatment of diseases. Such prevention or treatment preferably comprises (i) the administration of the periostin compound to the subject suffering from the haematological disorder, or (ii) in vitro treating a biological cell with the periostin compound and administering the so periostin-compound-treated cell to the subject suffering from the haematological disorder. Different routes for administration of periostin compounds will be described herein elsewhere.

In addition, the present invention shall also include compounds for use in the herein described preventions and treatments, wherein such compounds are agonists of periostin expression in a subject or in cells of a subject. Such compound may be any molecule known to the skilled person that is able to enhance periostin expression in a biological cell, which can either be a biological cell within a subject to be treated (in vivo) or alternatively in a biological in cell culture (ex vivo), for example a previously obtained HSC in context of HSCT. In this aspect of the invention the term "periostin agonist" shall be understood to refer to such a compound, and can be a substance selected from the following: polypeptide, peptide, glycoprotein, a peptidomimetic, an antigen binding construct (for example, an antibody, antibody-like molecule or other antigen binding derivative, or an antigen binding fragment thereof), a nucleic acid such as a DNA or RNA, for example an antisense or inhibitory DNA or RNA, a ribozyme, an RNA or DNA aptamer, RNAi, siRNA, shRNA and the like, including variants or derivatives thereof such as a peptide nucleic acid (PNA), protein expression constructs, such as for expression of periostin compounds, small molecular compounds, or a genetic construct for targeted gene editing, such as a CRISPR/Cas9 construct and/or a guide nucleic acid (gRNA/sgRNA or gDNA/sgRNA) and/or tracrRNA. The basic rules for the design of CRISPR/Cas9 mediated gene editing approaches are known to the skilled artisan and for example reviewed in Wiles M V et al (Mamm Genome. 2015 October; 26 (9-10): 501-10) or in Savić N and Schwank G (Transl Res. 2016 February; 168:15-21).

In some preferred embodiments of the herein disclosed invention, the biological cell is an autologous or allogenic haematopoietic stem cell (HSC). In one embodiment, as used herein, the term "hematopoietic stem cell" or "HSC" as used herein, refers to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages, dendritic cells) and lymphocytes (common lymphoid progenitors, pre-B, pro-B, mature B, pre-T, pro-B, mature T and NKT lymphocytes and NK cells). It is also known in the art that hematopoietic stem cells can include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage, erythroid, megakaryocytic, myeloid and/or macrophage cell lineage. HSCs also refer to long term HSC (L T-HSC) and short-term HSC (ST-HSC). LT-HSC and ST-HSC are differentiated, for example, based on their cell surface marker expression such as described herein or known by the skilled person.

In context of the present invention the term "autologous" when referring to a cell transplant procedure, or cellular sample, shall refer to the use of such cells that are obtained for a subject, treated or altered in accordance with the invention, and subsequently used again in the same subject for treating or preventing a condition. In contrast thereto, the term "allogenic" shall refer to such cell preparations that are obtained from one subject and used in another one, wherein however the two subjects are ideally genetically matched in order to minimize immunological adverse events during the cellular transplantation.

In some embodiments of the invention, the HSC is derived from an umbilical cord blood sample or from a bone marrow sample or from a mobilized haematopoietic stem cell obtained from peripheral blood, or from a placenta. The present invention shall include all sources of HSC known to the skilled artisan.

In context of the herein disclosed invention, treating a biological cell with the periostin compound or a periostin agonist involves contacting the cell with the periostin compound for a period of time and under adequate conditions sufficient to increase vitamin K dependent γ-carboxylated periostin and thereby to induce and/or augment and/or increase integrin beta 3 binding of periostin on said cell.

Preferably, the nucleic acid encoding the periostin protein in accordance with the invention, or encoding the functional fragment or variant thereof, is introduced into and expressed in a biological cell, preferably an allogenic or autologous HSC. Such expression is preferably a recombinant expression.

As mentioned herein elsewhere the periostin protein or the variant thereof is preferably human periostin for example one of SEQ ID NO: 1 to 7.

A variant of a periostin protein is, in certain embodiments, a functional variant of a periostin protein. In other embodiments of the invention, the variant of periostin is selected from the group consisting of an ortholog or paralog of human periostin, and a functional fragment of a human periostin protein.

The term "ortholog" refers to homologs in different species that evolved from a common ancestral gene by speciation. Typically, orthologs retain the same, essentially the same or similar function despite differences in their primary structure (mutations). The term "paralog" refers to homologs in the same species that evolved by genetic duplication of a common ancestral gene. In many cases, paralogs exhibit related but not always similar function. The term "splice variant" refers to a related protein expressed from the same genomic locus as a parent protein, but having a different amino acid sequence based on a different exon composition due to differential splicing of the transcribed RNA.

Typically, a variant of the periostin protein of the invention comprises an amino acid sequence that is at least 60, 65, 70, 75, 80, 85, 90, 95, 96, 97, 98, 99% identical to an amino acid sequence of a human periostin isoform shown in any one of SEQ ID NO: 1 to 7.

In some embodiments a proteinaceaous periostin compound of the invention, or a variant of a periostin protein, is a polypeptide or protein comprising at least the periostin gamma carboxylated site of human periostin, such as, comprising an amino acid sequence that is at least 60, 65, 70, 75, 80, 85, 90, 95, 96, 97, 98, 99% identical to an amino acid sequence between amino acids 300 and 400, preferably 300 and 350 of SEQ ID NO: 1.

The periostin compounds described herein are in some embodiments for use in the treatment and prevention of haematological disorders. The term "haematological disorder" shall be understood to refer at least to a pathological condition selected from a haematological malignancy, a disease associated with a pathological haematopoietic stem cell (HSC) function, such as a disease associated with decreased/impaired haematopoiesis, or is a haematological adverse event caused by a primary treatment of the subject, for example with a primary therapeutic for another, for example non-haematological, disorder.

Preferably a haematological malignancy in context of the invention is selected from cancers that affect one or more of the blood, bone marrow, and lymph nodes, such as acute lymphoblastic leukemia (ALL), B cell acute lymphoblastic leukemia (B-ALL), acute myeloid leukemia (AML), chronic lymphocytic leukemia (CLL), chronic myeloid leukemia (CML), in particular BCR-Abl mutated CML, hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

In context of this invention a disease associated with pathological HSC function is preferably selected from any of the following disorders: hypo or hyperproliferative stem cell disorders, such as aplastic anemia, neutropenia, cytopenia, anemia, pancytopenia, agranulocytosis, thrombocytopenia, red cell aplasia, Blackfan-Diamond syndrome, due to drugs, radiation, or infection, immunosuppression in subjects with solid tumors, malignant melanoma, nonsmall cell lung cancer, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, Lymphoma, autoimmune diseases such as rheumatoid arthritis, diabetes type I, chronic hepatitis, multiple sclerosis, systemic lupus erythematosus, genetic (congenital) disorders, such as anemias, familial aplastic anemias, Fanconi's syndrome, Bloom's syndrome, pure red cell aplasia (PRCA), dyskeratosis congenita, Blackfan-Diamond syndrome, congenital dyserythropoietic syndromes, Shwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal haemoglobinuria, G6PD (glucose-6-phosphate dehydrogenase) variants 1, 2, 3, pyruvate kinase deficiency, congenital erythropoietin sensitivity deficiency, sickle cell disease and trait, thalassemia alpha, beta, gamma, methemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital leukocyte dysfunction syndromes, and others, selected from osteopetrosis, myeloscleros, acquired hemolytic anemias, acquired immunodeficiencies, infectious disorders causing primary or secondary, immunodeficiency bacterial, infections (e.g. Brucellosis, Listeriosis, tuberculosis, leprosy), parasitic infections (e.g. malaria, Leishmaniasis), fungal infections, disorders involving disproportions in lymphoid cells, impaired immune, impaired functions due to aging, phagocyte disorders, Kostmann's agranulocytosis, chronic granulomatous disease, Chediak-Higachi syndrome, Willams-Beuren syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, and alpha 1-antitrypsin deficiency.

Further, for the purposes of the present invention, the haematological adverse event is preferably an event caused by a treatment of the subject with an anti-cancer agent, such as a chemotherapeutic agent, or by a radiotherapy treatment, or by treatment with a vitamin-K antagonist, such as warfarin, fluindione, phenindione, acenocoumarol, dicoumarol, ethyl biscoumacetate, or phenprocoumon, preferably in a subject suffering from or suspected to develop thromboembolic complications.

A prevention or treatment in context of the present invention preferably involves HSC transplantation (HSCT).

Furthermore, a treatment or prevention in accordance with the invention involves the administration of a periostin compound to the subject immediately before HSCT, such as preferably 5 to 1 days before HSCT, more preferably about 3-2 days before HSCT; or concomitant with the HSCT, and/or immediately after HSCT, preferably until full engraftment of the HSC in the treated subject.

The periostin compound according to the invention is in some embodiments additionally used to prepare/treat a HSC transplant before transplantation. For example the HSCs prior to transplantation in a subject are contacted with a periostin compound as described herein. Such a procedure will induce and activate the HSC in the preparation resulting in an improved HSC transplant and improved treatment success.

Yet another embodiment then pertains to a pharmaceutical composition comprising a periostin compound selected from a periostin protein, or a functional fragment or variant thereof, or a periostin nucleic acid encoding the periostin protein, or encoding the functional fragment or variant thereof, and a pharmaceutically acceptable carrier and/or excipient.

The pharmaceutical compositions described herein are preferably indicated for the use in the prevention or treatment of a haematological disorder as described, or indicated for use to improve haematopoiesis in a stem cell donor subject.

As used herein the language "pharmaceutically acceptable" carrier, stabilizer or excipient is intended to include any and all solvents, solubilizers, fillers, stabilizers, binders, absorbents, bases, buffering agents, lubricants, controlled release vehicles, diluents, emulsifying agents, humectants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application, as well as comprising a compound of the invention (eg a periostin compound), can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Kolliphor® EL (formerly Cremophor EL™; BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of the invention (e.g., a periostin compound) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, as well as comprising a compound of the invention (eg a periostin compound), generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

Furthermore, the compounds of the invention (eg a periostin compound) can be administrated rectally. A rectal composition can be any rectally acceptable dosage form including, but not limited to, cream, gel, emulsion, enema, suspension, suppository, and tablet. One preferred dosage form is a suppository having a shape and size designed for introduction into the rectal orifice of the human body. A suppository usually softens, melts, or dissolves at body temperature. Suppository excipients include, but are not limited to, theobroma oil (cocoa butter), glycerinated gelatin, hydrogenated vegetable ails, mixtures of polyethylene glycols of various molecular weights, and fatty acid esters of polyethylene glycol.

For administration by inhalation, the compounds of the invention (eg a periostin compound) are typically delivered in the form of an aerosol spray from pressured container or dispenser which contains a suitable propellant, e.g., a gas such as carbon dioxide, or a nebulizer.

Systemic administration can also be by transmucosal or transdermal route and/or (other) means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions can be formulated into ointments, salves, gels, or creams as generally known in the art.

In certain embodiments, the pharmaceutical composition is formulated for sustained or controlled release of a compound of the invention (e.g., a periostin compound). Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially (including liposomes targeted to infected cells with monoclonal antibodies to viral antigens) can also be used as pharmaceutically acceptable carriers. These can be prepared according to methods known to those skilled in the art.

It is especially advantageous to formulate oral, rectal or parenteral compositions in dosage unit form for case of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage of the compound of the invention (e.g., a periostin compound) for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the therapeutic approaches of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

Yet another aspect of the invention pertains to a method for manufacturing a medicament for the prevention or treatment of a haematological disorder, the method comprising the steps of formulating a periostin compound as described, together with a pharmaceutically acceptable carrier and or excipient.

The problem of the invention is solved in an additional aspect by a method for preparing or improving a stem cell transplant, the method comprising the steps of
(a) Providing a composition of stem cells,
(b) Contacting the composition of stem cells with a periostin compound as described herein elsewhere,
(c) Incubating the mixture of b for a sufficient amount of time to obtain a suitable stem cell transplant
(d) Optionally, culturing and/or purifying the stem cell transplant.

The term "transplant" or "stem cell transplant" or "HSC transplant" or similar expression shall refer to a preparation of stem cells intended for and/or suitable for transplantation into a subject, preferably for therapeutic reasons.

The method for preparing or improving a stem cell transplant in accordance with the present invention in some embodiments is a method wherein all steps are performed ex vivo/in vitro.

A stem cell transplant prepared or treated according to the above described method has improved activity during a stem cell transplantation.

Stem cells to be used in the preparation method are preferably HSC, preferably HSC derived from an umbilical cord blood sample or from a bone marrow sample or from human placenta. In context of the present invention any applicable source for HSC may be used. A review of HSC sources and their applicability if for example provided in Br J Haematol. 2009 October; 147 (2): 246-261, which is incorporated herein in its entirety by reference.

Yet another aspect of the invention pertains to a method for improving haematopoietic stem cell (HSC) function/activity, the method comprising contacting the HSC with a sufficient amount of a periostin compound as described herein elsewhere.

A method for treating a subject suffering from an impaired or decreased haematopoiesis, the method comprising administering to the patient a therapeutically effective amount of at least one of:
a. A periostin compound or agonist as described herein elsewhere; or
b. A biological cell, preferably a HSC, which was before brought into contact with (primed with) a periostin compound as described. The modes and preferences of administration of periostin compounds or agonists of the invention are the same as described herein elsewhere.

A subject to be treated by a treatment or prevention of the invention is preferably a mammal, preferably a human, most preferably a human patient, for example a human of 40, 50, 60 years of age or older.

Further, the invention provides in one additional aspect a method for enhancing haematopoiesis in a donor-subject to improve or prepare a stem cell donation of the subject, the method comprising administering to the donor-subject a periostin compound selected from a periostin protein, or a functional fragment or variant thereof, or a periostin nucleic acid encoding the periostin protein, or encoding the functional fragment or variant thereof. This method is in preferred embodiments a non-therapeutic method, meaning that the method is performed with the intention to improve the natural or normal haematopoiesis in the donor-subject solely for obtaining stem cells from the donor-subject. These stem cells may then be used in any of the therapeutic or preventive aspects of the herein disclosed invention, or other medical application where such stem cell preparations are useful or needed. The method shall be understood to be not for treating or preventing a disease or disorder in the donor-subject. Insofar this method preferably does not include any extensive surgical step. In other embodiments, where such surgical steps are necessary, it is preferred that the periostin compound is for use in the herein described method for enhancing haematopoiesis in a donor-subject.

In accordance with the findings of the herein disclosed invention the described method is for improving the quality and/or quantity of a stem cell donation obtained from the donor-subject.

A "donor-subject" in context of the invention shall be understood to refer to a mammal, preferably a human, from which stem cells are obtained in order to prepare stem cell transplantation. In some embodiments, where autologous stem cells are used in any of the herein disclosed applications, the donor-subject and the subject to be treated with the stem cells are the same person, however, receiving two separate treatments, one of non-therapeutic nature, and then the back-transplantation of the stem cells, which is of a therapeutic nature. In other embodiments, where a heterologous/allogenic transplant is prepared, a donor-subject is not identical to the subject to be treated. However, it might be preferable that the donor-subject is at least related or genetically matched to the subject to be treated in order to minimize adverse immunological events such as a transplant rejection.

Yet a further aspect of the invention provides a method for obtaining stem cells from a donor-subject, the method comprising the steps of.
  a. administering to the donor-subject a periostin compound selected from a periostin protein, or a functional fragment or variant thereof, or a periostin nucleic acid encoding the periostin protein, or encoding the functional fragment or variant thereof,
  b. harvesting stem cells from the donor-subject.

In some embodiments the method may comprise the additional administration of a cell adhesion inhibitor to the donor-subject, preferably one or more compounds selected from Plerixafor, CTCE-9908, a thiopseudourea compound, TN14003, KRH-2731, KRH-3955, TC14012, AMD070, BKT-140, neutrophil elastase, and cathepsin G.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Warfarin compromises hematopoiesis and HSC function. A and B) Total number of leukocytes ($P=0.008$ and $P=0.002$; t-test, n=5) (A) and monocytes ($P=0.007$ and $P=0.001$; t-test, n=5) (B) in peripheral blood of control mice (black) or mice treated with 0.5 mg/kg (white) or 0.05 mg/kg (gray) warfarin 14 days after begin of treatment. C) Percentage of CD11b+ myeloid cells in peripheral blood ($P=0.029$; t-test, n=3). D) Number of colonies in methylcellulose from BM cells from vehicle (black)- or warfarin (white)-treated mice ($P=0.02$, t-test). E-F) Total number of leukocytes ($P=0.029$) 7 days after a one-time treatment with 200 mg/kg 5-fluorouracil (E) and Kaplan-Meier-style survival curve (F) of control mice (solid line) or mice treated with 0.5 mg/kg (dashed line) ($P=0.0004$; Log-rank test, n=8) or 0.05 mg/kg warfarin (dotted line) ($P=0.016$; Log-rank test, n=5) cotreated with 75 mg/kg 5-fluorouracil on days 0, 7, 14, 21. G-I) Competitive (P values as indicated; t-test, n=5) (G), serial (P values as indicated; t-test, n=5) (H) and limiting dilution ($P=0.0006$) (I) transplantation assays using CD45.1+ total donor bone marrow from control (solid line) mice or warfarin (dashed line)-treated mice. The limiting dilution assay (I) shows the percentage of non-engrafted mice (y-axis) in relation to the dose of transplanted bone marrow. The lines fitted by regression analysis (L-Calc) allow estimation of functional HSC frequency, which was 7.6 fold lower in warfarin-treated donors. (J) Number of colonies arising from Lin-bone marrow cells pretreated with vehicle or 2 μM warfarin for 7 days plated in methylcellulose in the absence of drugs. Colonies were scored on day 10 after plating.

Figure 2:
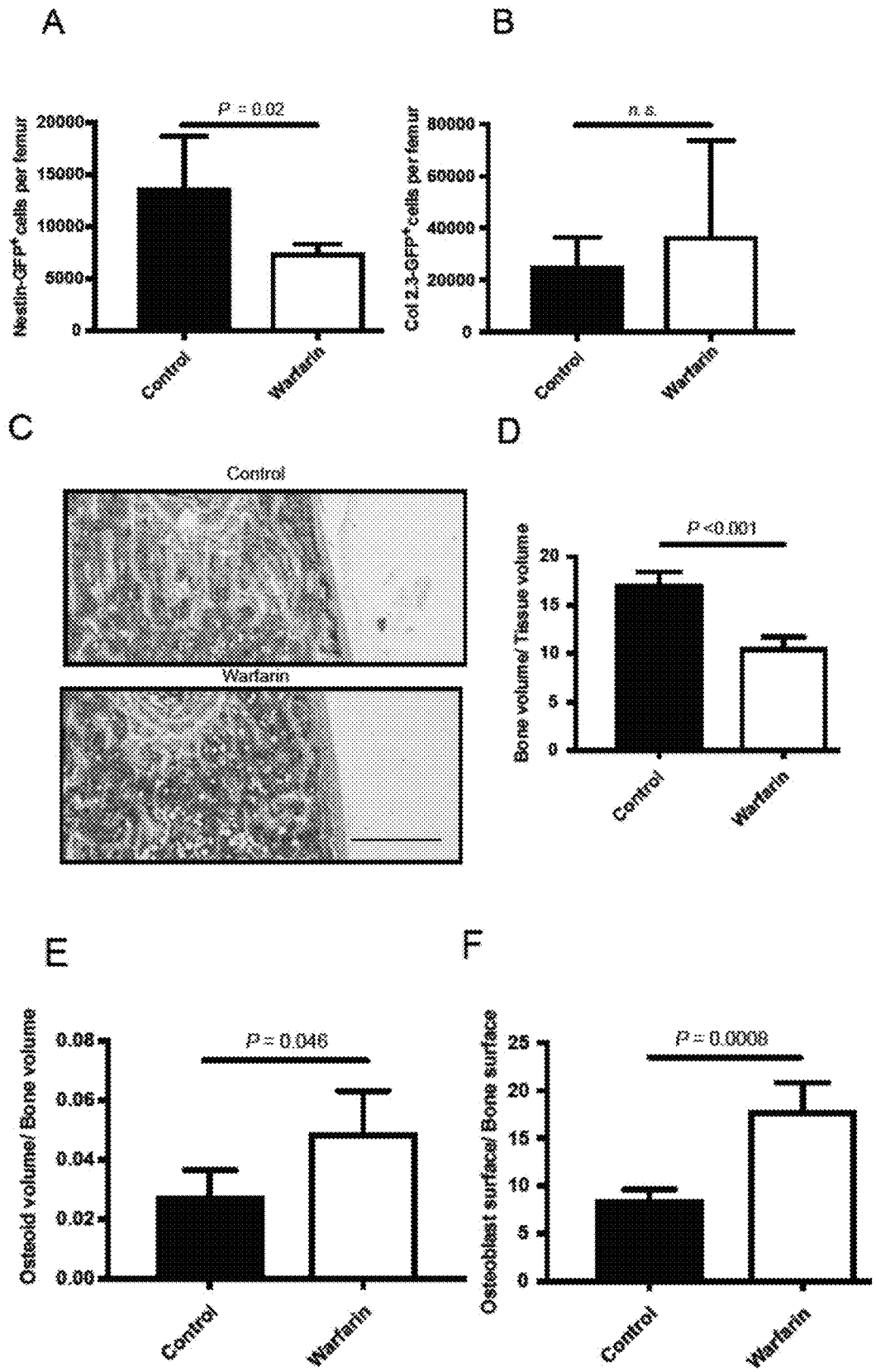
Figure 2:
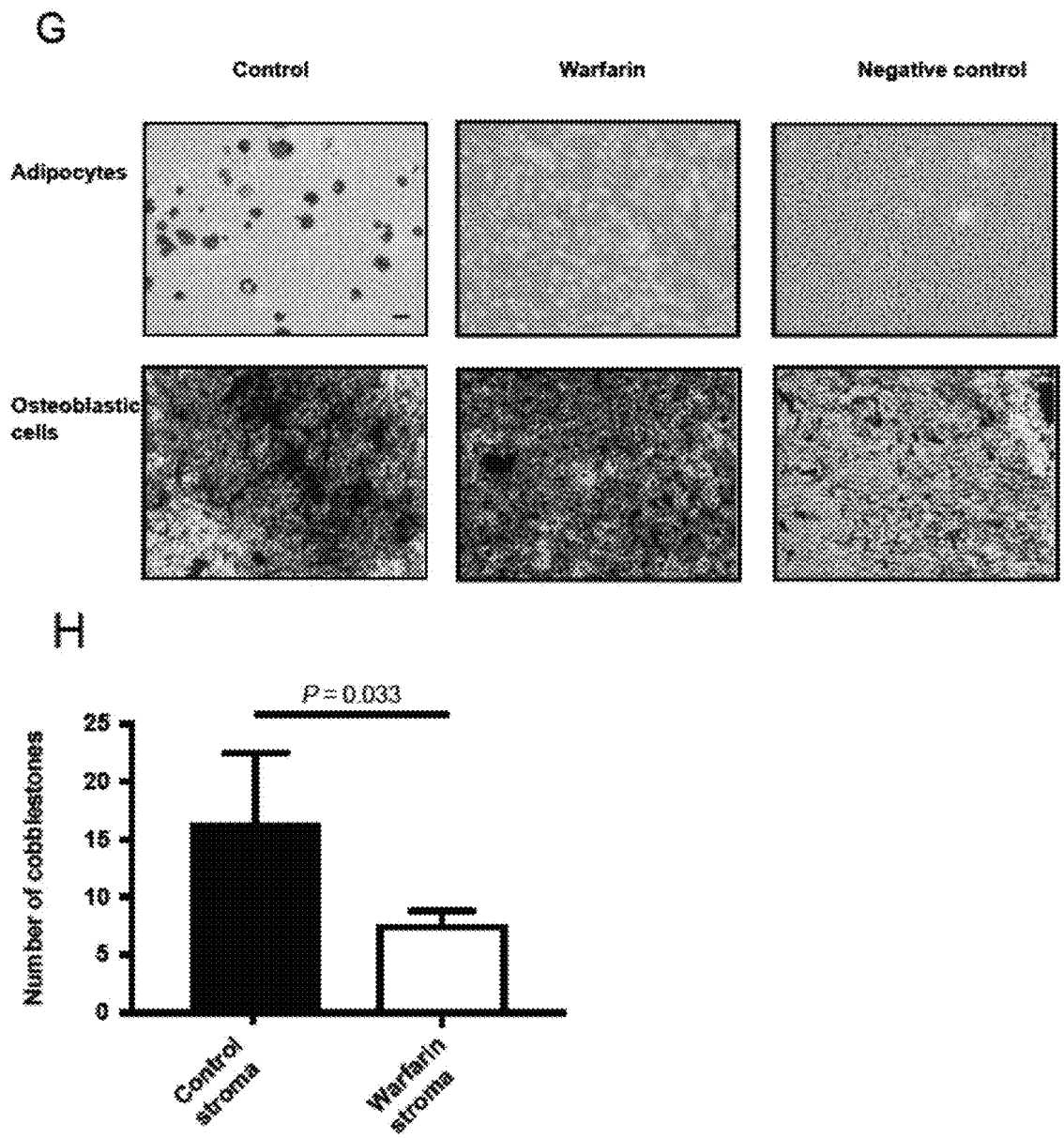

FIG. 2: Warfarin impairs bone marrow stroma. A-B) Number of Nestin+ MSC ($P=0.02$; t-test, n=5) (A) or Col2.3 kb GFP+ osteoblastic cells (n.s.; t-test, n=4) (B) in crushed, collagenase-treated bones of Nestin-GFP− (A) or Col2.3 kb GFP+ (B) control mice (black) or mice treated with warfarin (white) for 14 days. C) Trichrome stain of the distal femora of a representative control versus a warfarin-treated mouse. Note the dramatic reduction in cancellous bone in warfarin-treated animal compared to vehicle control. D-F) Ratios of bone volume/tissue volume ($P<0.001$; t-test, n=4-5) (D), osteoid volume/bone volume ($P=0.046$; t-test, n=4-5) (E) and osteoblast surface/bone surface ($P=0.0008$; t-test, n=4-5) (F) in control (black) versus warfarin-treated (white). G) Differentiation of primary murine stroma cells into adipocytes (top) or osteoblastic cells (bottom) in the presence of vehicle or warfarin or in the absence of differentiation factors (control). Oil Red O stains adipocytes red, while von Kossa stains osteoblastic cells brown. The scale bar depicts 100 μm. H) Number of cobblestones formed by Lin− cells under stroma which had been treated with vehicle (black) or warfarin (white) for 10 days ($P=0.033$; t-test).

Figure 3:
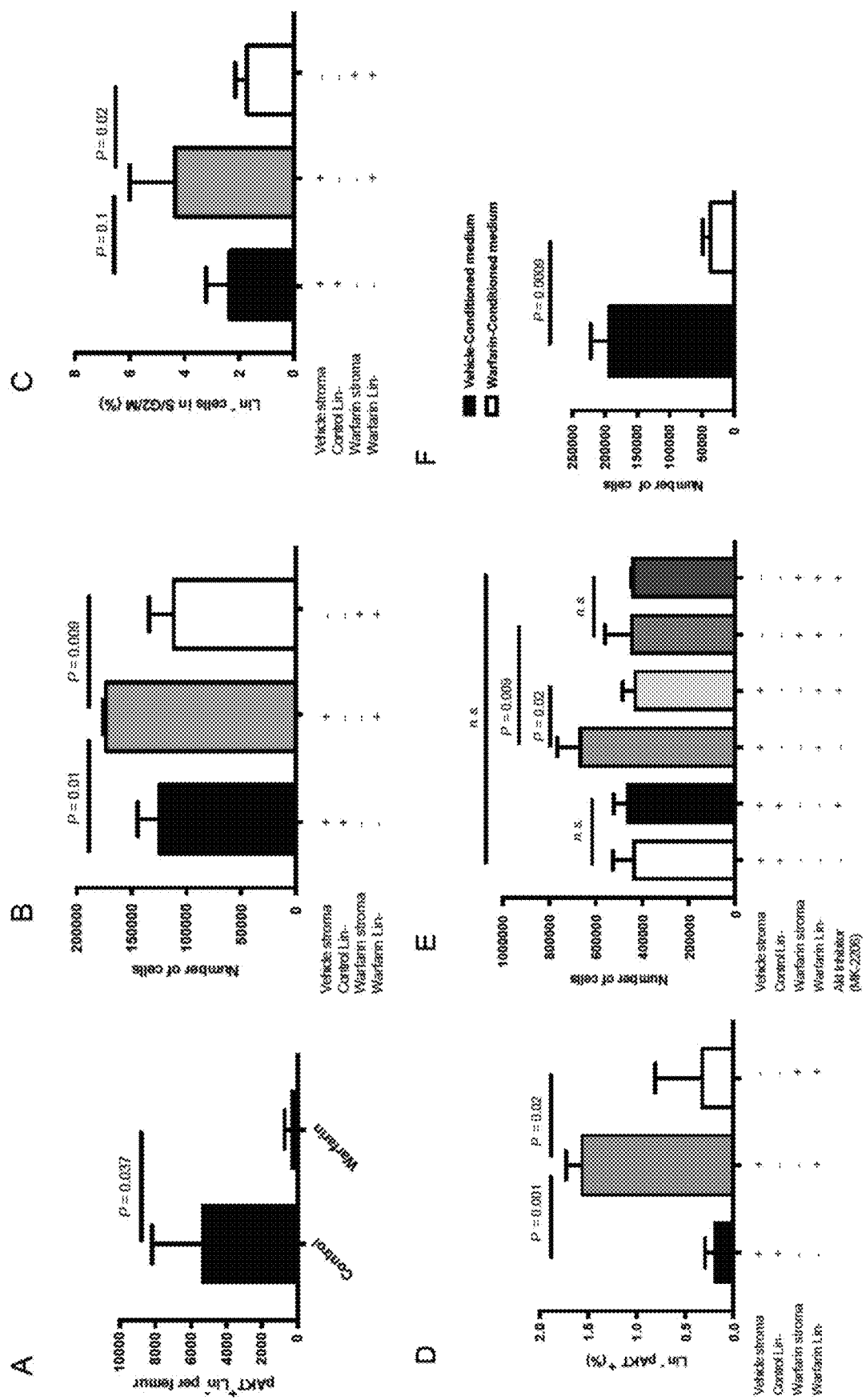
Figure 3:
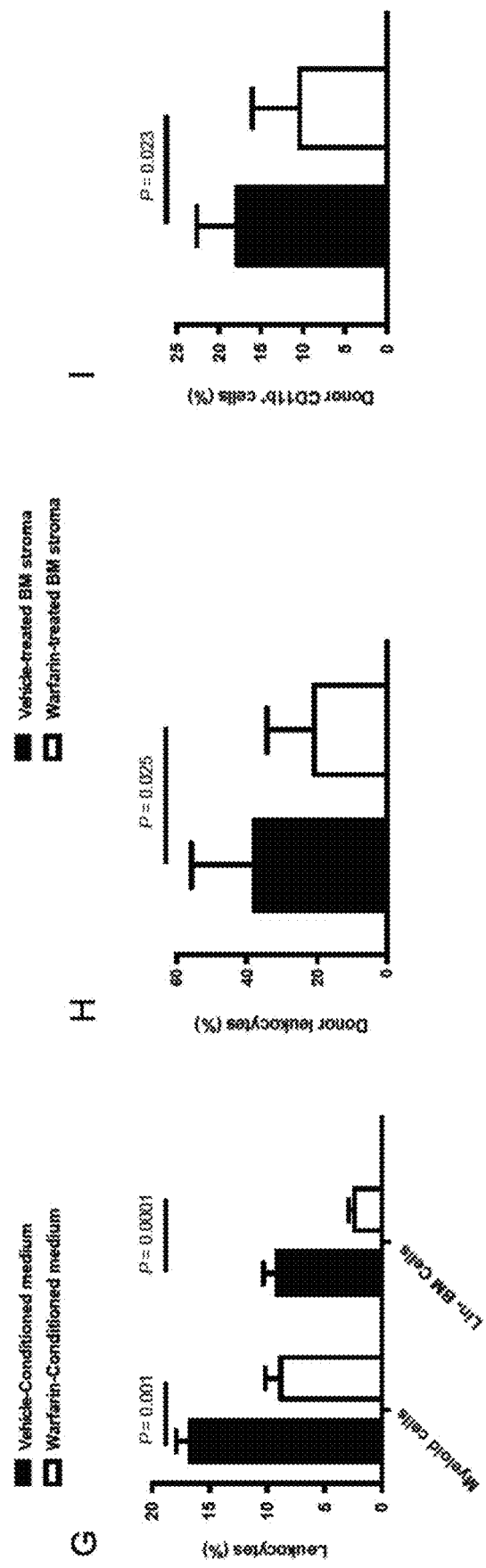

FIG. 3: Warfarin reversibly impairs the HSC-supportive function of bone marrow stroma via a pAKT-dependent mechanism in HSC. A) Number of Lin− pAKT+ cells in the bone marrow of control mice or mice treated with warfarin 14 days after initiation of treatment ($P=0.037$, t-test, n=4).). B) Total number of hematopoietic cells two days after plating of Lin− cells from vehicle- or warfarin-treated mice on vehicle- or warfarin-treated stroma ($P=0.009$, t-test, n=3). C) Percentage of Lin− cells in the S/G2/M phase of the cell cycle 7 days after plating of Lin− cells from vehicle- or warfarin-treated mice on vehicle (gray)- or warfarin (white)-treated stroma ($P=0.02$, t-test, n=3). D) Percentage of Lin− pAKT+ cells 3 days after plating of Lin− cells from vehicle- or warfarin-treated mice on vehicle (gray)- or warfarin (white)-treated stroma ($P=0.02$, t-test, n=3). E) Total number of hematopoietic cells four days after plating of Lin− cells from vehicle- or warfarin-treated mice on vehicle- or warfarin-treated stroma in the presence of the AKT inhibitor MK-2206 (5 μM) ($P=0.02$, t-test, n=5). F-G) Total number of hematopoietic cells ($P=0.0009$; t-test, n=3) (F) and percentage of myeloid ($P=0.001$) and Lin− cells ($P=0.0001$) (G) grown in conditioned medium harvested from stroma cells grown in vehicle (black)- or warfarin (white)-containing medium 3 days after plating of Lin− cells. H-I) Percentage of total donor Actin DsRed+ leukocytes ($P=0.025$; t-test, n=10) (H) and percentage of donor CD11b+ Actin DsRed+ myeloid cells ($P=0.023$; t-test, n=8) (I) in recipients, which had been intrafemorally cotransplanted with untreated Actin DsRed+ Lin− and vehicle (black)- or warfarin (white)-pretreated stroma cells 6-8 weeks previously. The stroma had, originally, been obtained from warfarin-treated mice and expanded in the continuous presence of warfarin in vitro.

Figure 4:
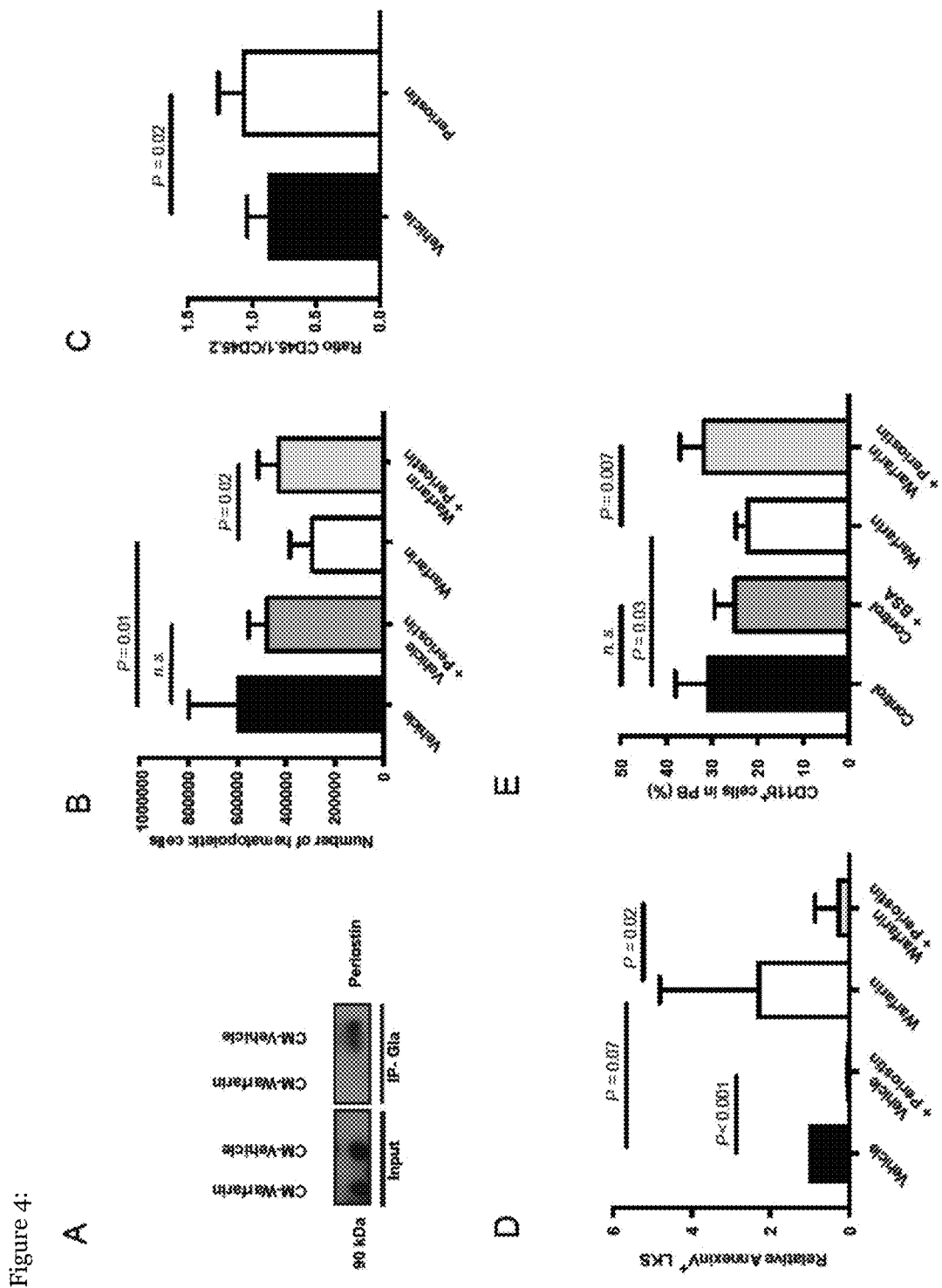

FIG. 4: Warfarin impairs hematopoiesis via periostin. A) Co-immunoprecipitation of concentrated conditioned medium (CM) from vehicle- or warfarin-treated stroma cells with an anti-Gla antibody. The Western blot was performed with an antibody to periostin (90 kDa). B) Total number of hematopoietic cells in an in vitro co-culture of vehicle (black)- or warfarin (white)-treated stroma cells and hematopoietic cells from murine bone marrow, to which 2 μg/ml periostin (lighter gray) had been added. The increase of the number of hematopoietic cells ($P=0.02$, t-test, n=6) 5 days after addition of periostin is significant. C) Ratio of CD45.1/CD45.2 four weeks after competitive transplantation of CD45.1+ total donor bone marrow from vehicle (black)- or periostin (white)-treated mice, mixed with CD45.2+ competitor cells and transplanted into CD45.2+ recipient mice ($P=0.02$; t-test, n=10). D) Abundance of annexin+ DAPI+ LKS cells in mice treated with vehicle (black) or warfarin (white) and periostin (lighter gray) relative to vehicle-treated mice ($P=0.02$; t-test, n=10). E) Percentage of CD11b+ myeloid cells in the peripheral blood of mice treated with control (black)- or warfarin (white) plus BSA (dark gray) or periostin (light gray). The increase of the percentage of myeloid cells ($P=0.007$, t-test, n=5) after a 4 day treatment with periostin is significant.

Figure 5:
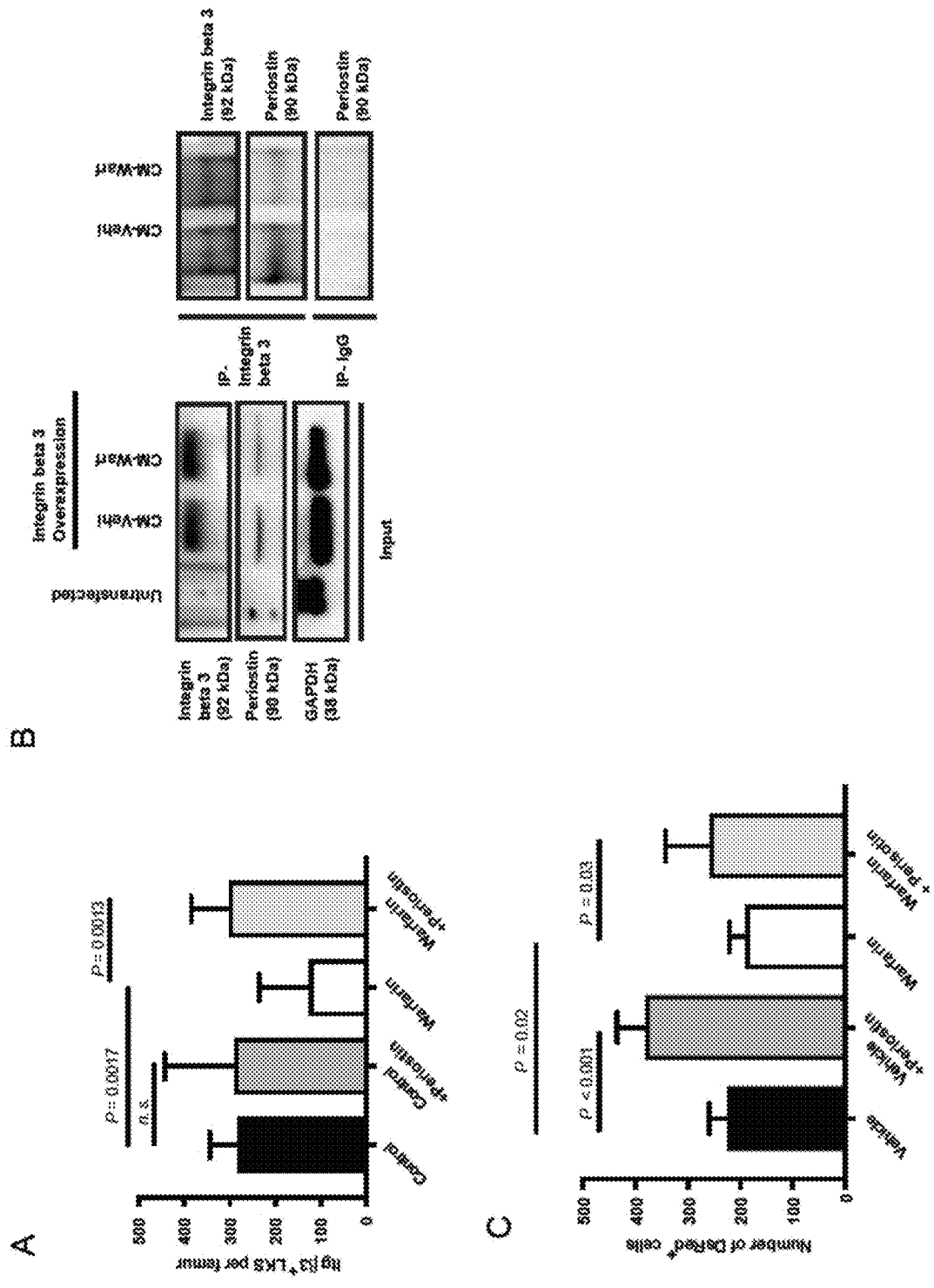

FIG. 5: Warfarin impairs hematopoiesis via the periostin/integrin β3 axis. A) Number of LKS cells expressing integrin β3 in mice treated with vehicle (black) or warfarin (white) for 4 weeks and periostin (lighter gray) ($P=0.0013$; t-test, n=10). B) Protein lysates of 293T cells, transfected with an integrin β3-overexpressing construct and grown in conditioned medium from vehicle- or warfarin-treated stroma cells, were subjected to coimmunoprecipitation with an anti-integrin β3 antibody, and coimmunoprecipitation of periostin was assessed by immunoblotting, as indicated. Anti-IgG-isotype antibody was used as control in the co-immunoprecipitation. The input (left) shows the presence of integrin β3 (92 kDa) and periostin (90 kDa), and GAPDH (38 kDa) was used to control for equal loading. C) Adhesion of 100,000 Lin– Actin– DsRed+ cells to vehicle- or warfarin-treated stroma cells in the presence or absence of periostin (P=0.03; t-test).

Figure 6:
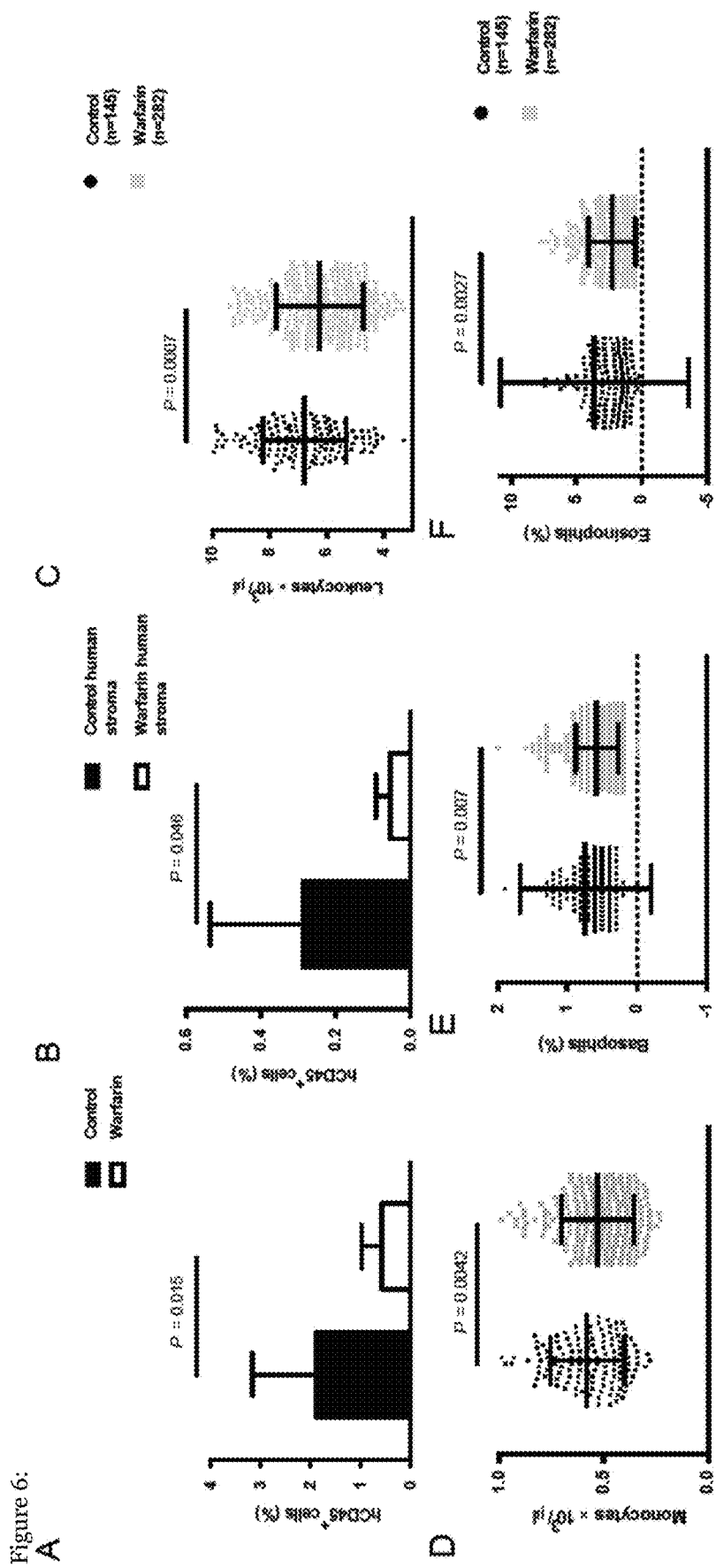
Figure 6:
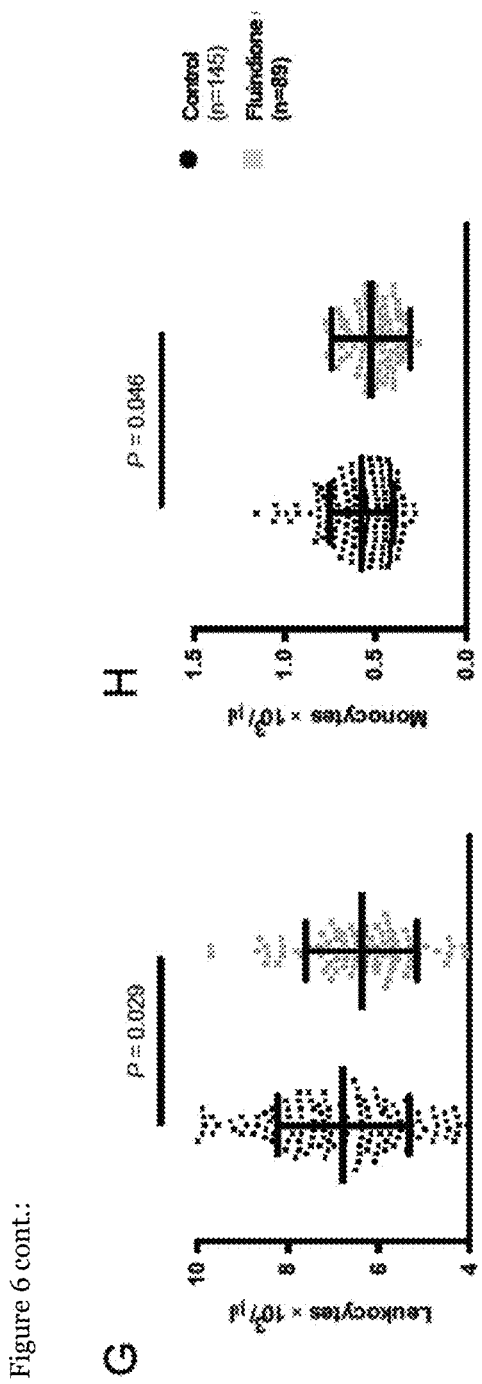

FIG. 6: Vitamin K antagonism leads to reduction of human leukocytes and engraftment of human HSC. A) Percentage of human CD45+ leukocytes in the peripheral blood of vehicle (black)- or warfarin (white)-treated NSG mice 6 weeks after transplantation with $1.3 \times 10^5$ human CD34+ HSC (P=0.015, t-test, n=9). B) Percentage of human CD45+ leukocytes in the peripheral blood of NSG mice 4 weeks after intrafemoral co-transplantation of $0.8 \times 10^5$ human CD34+ HSC and $5 \times 10^5$ vehicle (black)- or warfarin (white)-treated human autologous stroma cells (P=0.046, t-test, n=6). C-D) Total number of leukocytes (P=0.0007, t-test) (C) and monocytes (P=0.0042, t-test) (D) in the peripheral blood of control patients (black; n=145) and patients on warfarin (white; n=282). E-F) Percentage of basophils (P=0.007, t-test) (E) and eosinophils (P=0.0027, t-test) (F) of all leukocytes in the peripheral blood of control patients (black; n=145) and patients on warfarin (white; n=282). G-H) Total number of leukocytes (P=0.029, t-test) (G) and monocytes (P=0.046, t-test) (H) in the peripheral blood of control patients (black; n=145) and patients on fluindione (white; n=89), another vitamin K-antagonist similar to warfarin.

Figure 7:
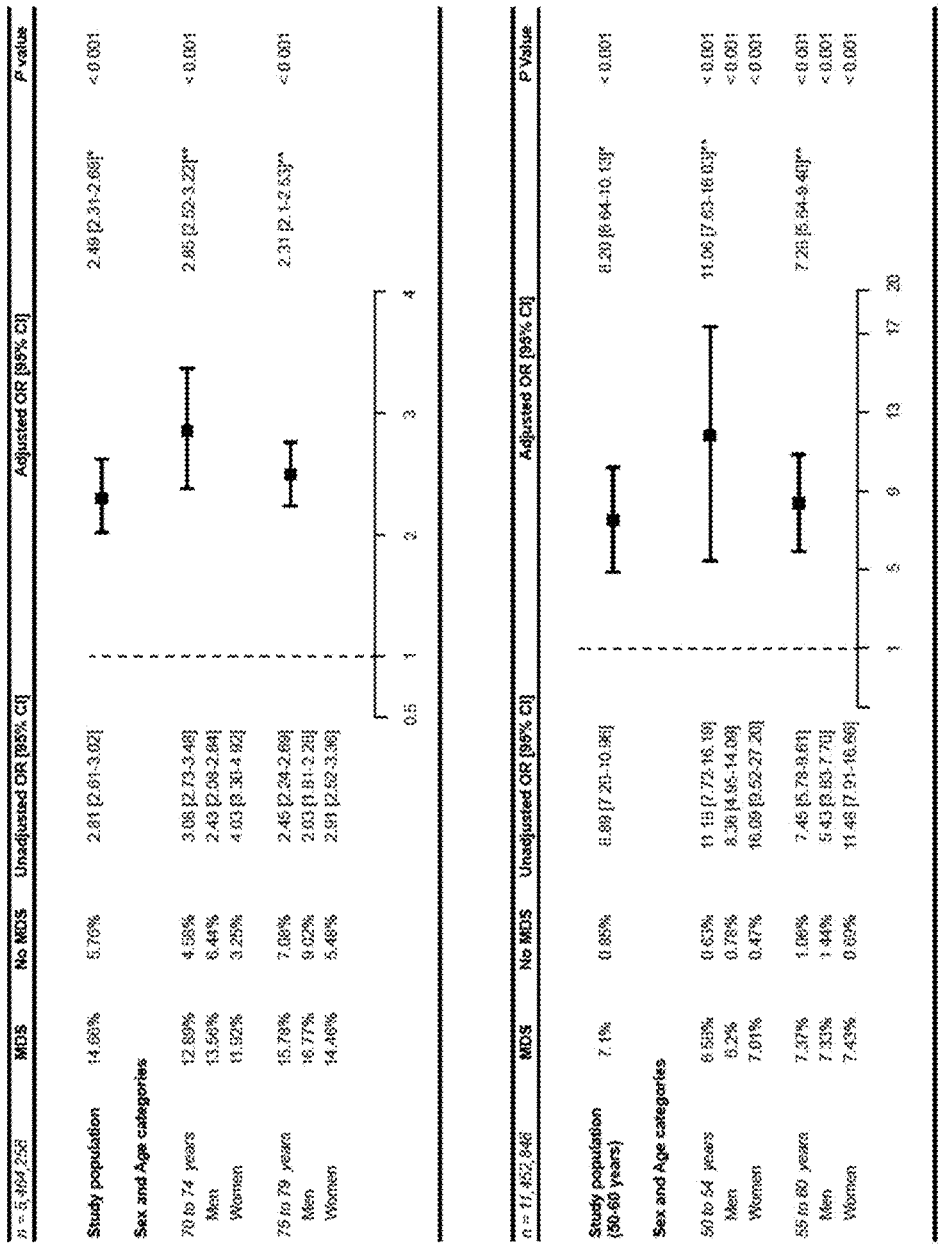

FIG. 7: A-B) Use of vitamin K antagonists (VKA) in men and women aged 70-79 years (n=5,464,258) (A) or 50-60 years (n=11,452,848) (B) with and without a diagnosis of myelodysplastic syndrome (MDS) in 2015. Data source: French health-care databases.

Figure 8:
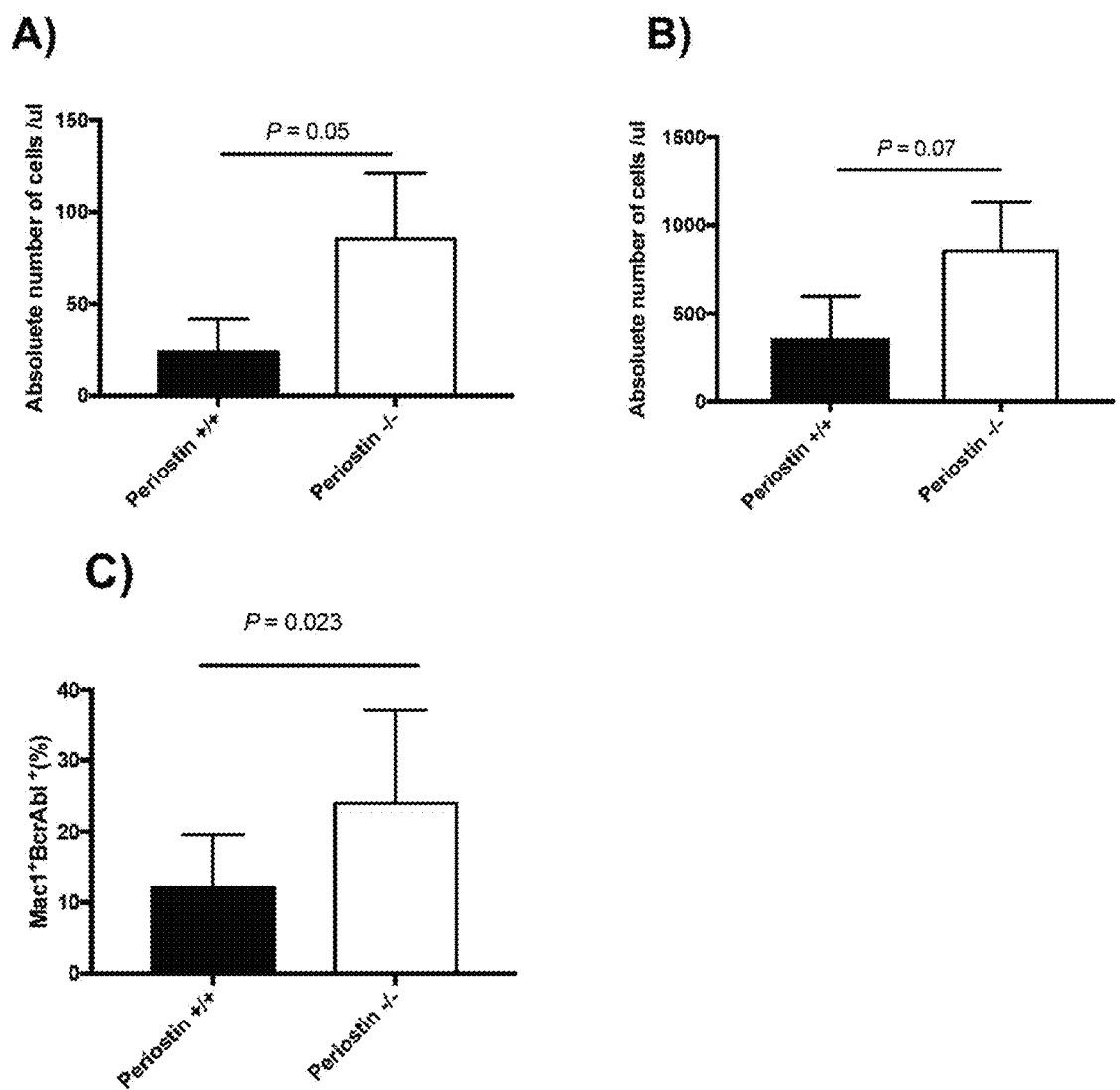

FIG. 8: A-B) Total number of hematopoietic cells in an in vitro co-culture of (A) K562 (P=0.05; t-test, n=3) and (B) BCR-ABl1+ Baf3 (P=0.07; t-test, n=3) leukemic cells on wildtype (black)-versus periostin deficient (white) bone marrow stroma cells. (C) Percentage of Mac-1 (CD11b)+ BCR-ABL1+ leukemic cells in the peripheral blood of wildtype (black) or periostin-deficient (white) recipient mice intravenously transplanted with transduced bone marrow (P=0.02; t-test, n=10).

And in the sequences:

```
SEQ ID NO: 1 Human Periostin Isoform 1, also known
     as OSF-2OS (Uniprot Identifier: Q15063-1)
        10         20         30         40         50
MIPFLPMFSL LLLLIVNPINANNHYDKILAHSRIRGRDQGPNVCALQQIL 60         70         80         90        100
GTKKKYFSTC KNWYKKSICGQKTTVLYECCPGYMRMEGMKGCPAVLPIDH 110        120        130        140        150
VYGTLGIVGA TTTQRYSDASKLREEIEGKGSFTYFAPSNEAWDNLSDIR 160        170        180        190        200
RGLESNVNVE LLNALHSHMINKRMLTKDLKNGMIIPSMYNNLGLFINHYP 210        220        230        240        250
NGVVTVNCAR IIHGNQIATNGVVHVIDRVLTQIGTSIQDFIEAEDDLSSF
```

```
SEQ ID NO: 1 Human Periostin Isoform 1, also known
     as OSF-2OS (Uniprot Identifier: Q15063-1)
       260        270        280        290        300
RAAAITSDIL EALGRDGHFTLFAPTNEAFEKLPRGVLERIMGDKVASEAL 310        320        330        340        350
MKYHILNTLQ CSESIMGGAVFETLEGNTIEIGCDGDSITVNGIKMVNKKD 360        370        380        390        400
IVTNNGVIHL IDQVLIPDSAKQVIELAGKQQTTFTDLVAQLGLASALRPD 410        420        430        440        450
GEYTLLAPVN NAFSDDTLSMDQRLLKLILQNHILKVKVGLNELYNGQILE 460        470        480        490        500
TIGGKQLRVF VYRTAVCIENSCMEKGSKQGRNGAIHIFREIIKPAEKSLH 510        520        530        540        550
EKLKQDKRFS TELSLLEAADLKELLTQPGDWTLFVPTNDAFKGMTSEEKE 560        570        580        590        600
ILIRDKNALQ NIILYHLTPGVFIGKGFEPGVTNILKTTQGSKIFLKEVND 610        620        630        640        650
TLLVNELKSK ESDIMTTNGVIHVVDKLLYPADTPVGNDQLLEILNKLIKY 660        670        680        690        700
IQIKFVRGST FKEIPVTVYTTKIITKVVEPKIKVIEGSLQPIIKTEGPTL 710        720        730        740        750
TKVKIEGEPE FRLIKEGETITEVIHGEPIIKKYTKIIDGVPVEITEKETR 760        770        780        790        800
EERIITGPEI KYTRISTGGGETEETLKKLLQEEVTKVTKFIEGGDGHLFE 810        820        830
DEEIKRLLQG DTPVRKLQANKKVQGSRRRLREGRSQ
```

```
SEQ ID NO: 2 Human Periostin Isoform 2, also known
     as OSF-2p1 (Uniprot Identifier: Q15063-2)
        10         20         30         40         50
MIPFLPMFSLLLLLIVNPIN ANNHYDKILA HSRIRGRDQGPNVCALQQIL 60         70         80         90        100
GTKKKYFSTCKNWYKKSICG QKTTVLYECC PGYMRMEGMKGCPAVLPIDH 110        120        130        140        150
VYGTLGIVGATTTQRYSDAS KLREEIEGKG SFTYFAPSNEAWDNLSDIR 160        170        180        190        200
RGLESNVNVELLNALHSHMI NKRMLTKDLK NGMIIPSMYNNLGLFIN-
                                                  HYP 210        220        230        240        250
NGVVTVNCARIIHGNQIATN GVVHVIDRVL TQIGTSIQDFIEAED-
                                                  DLSSF 260        270        280        290        300
RAAAITSDILEALGRDGHFT LFAPTNEAFE KLPRGVLERIMGDK-
                                                  VASEAL 310        320        330        340        350
MKYHILNTLQCSESIMGGAV FETLEGNTIE IGCDGDSITVNGIKMVNKKD 360        370        380        390        400
IVINNGVIHLIDQVLIPDSA KQVIELAGKQ QTTFTDLVAQLGLA-
                                                  SALRPD 410        420        430        440        450
GEYTLLAPVNNAFSDDTLSM DQRLLKLILQ NHILKVKVGLNELYN-
                                                  GQILE 460        470        480        490        500
TIGGKQLRVFVYRTAVCIEN SCMEKGSKQG RNGAIHIFREIIK-
                                                  PAEKSLH
```

SEQ ID NO: 2 Human Periostin Isoform 2, also known
as OSF-2p1 (Uniprot Identifier: Q15063-2)

```
        510        520        530        540        550
EKLKQDKRFSTELSLLEAAD LKELLTQPGD WTLFVPTNDAFKGMT-
                                                SEEKE
        560        570        580        590        600
ILIRDKNALQNIILYHLTPG VFIGKGFEPG VTNILKTTQGSKI-
                                           FLKEVND
        610        620        630        640        650
TLLVNELKSKESDIMTINGV IHVVDKLLYP ADTPVGNDQLLEILNK-
                                              LIKY
        660        670        680        690        700
IQIKFVRGSTFKEIPVTVYK PIIKKYTKII DGVPVEITEKETREERIITG
        710        720        730        740        750
PEIKYTRISTGGGETEETLK KLLQEEVTKV TKFIEGGDGHLFEDEE-
                                             IKRL
        760        770
LQGDTPVRKLQANKKVQGSR RRLREGRSQ
```

SEQ ID NO: 3 Human Periostin Isoform 3
(Uniprot Identifier: Q15063-3)

```
        10         20         30         40         50
MIPFLPMFSLLLLLIVNPINANNHYDKILA HSRIRGRDQGPNVCALQQIL
        60         70         80         90         100
GTKKKYFSTCKNWYKKSICGQKTTVLYECC PGYMRMEGMKGCPAVLPIDH
        110        120        130        140        150
VYGTLGIVGATTTQRYSDASKLREEIEGKG SFTYFAPSNEAWDNLDSDIR
        160        170        180        190        200
RGLESNVNVELLNALHSHMINKRMLTKDLK NGMIIPSMYNNLGLFINHYP
        210        220        230        240        250
NGVVTVNCARIIHGNQIATNGVVHVIDRVL TQIGTSIQDFIEAEDDLSSF
        260        270        280        290        300
RAAAITSDILEALGRDGHFTLFAPTNEAFE KLPRGVLERIMGDKVASEAL
        310        320        330        340        350
MKYHILNTLQCSESIMGGAVFETLEGNTIE IGCDGDSITVNGIKMVNKKD
        360        370        380        390        400
IVTNNGVIHLIDQVLIPDSAKQVIELAGKQ QTTFTDLVAQLGLASALRPD
        410        420        430        440        450
GEYTLLAPVNNAFSDDTLSMDQRLLKLILQ NHILKVKVGLNELYNGQILE
        460        470        480        490        500
TIGGKQLRVFVYRTAVCIENSCMEKGSKQG RNGAIHIFREIIKPAEKSLH
        510        520        530        540        550
EKLKQDKRFSTELSLLEAADLKELLTQPGD WTLFVPTNDAFKGMTSEEKE
        560        570        580        590        600
ILIRDKNALQNIILYHLTPGVFIGKGFEPG VTNILKTTQGSKIFLKEVND
        610        620        630        640        650
TLLVNELKSKESDIMTTNGVIHVVDKLLYP ADTPVGNDQLLEILNKLIKY
        660        670        680        690        700
IQIKFVRGSTFKEIPVTVYRPTLTKVKIEG EPEFRLIKEGETITEVIHGE
        710        720        730        740        750
PIIKKYTKIIDGVPVEITEKETREERIITG PEIKYTRISTGGGETEETLK
        760        770        780
KLLQEDTPVRKLQANKKVQGSRRRLREGRS Q
```

SEQ ID NO: 4 Human Periostin Isoform 4
(Uniprot Identifier: Q15063-4)

```
        10         20         30         40         50
MIPFLPMFSL LLLLIVNPINANNHYDKILAHSRIRGRDQGPNVCALQQIL
        60         70         80         90         100
GTKKKYFSTC KNWYKKSICGQKTTVLYECCPGYMRMEGMKGCPAVLPIDH
        110        120        130        140        150
VYGTLGIVGA TTTQRYSDASKLREEIEGKGSFTYFAPSNEAWDNLDSDIR
        160        170        180        190        200
RGLESNVNVE LLNALHSHMINKRMLTKDLKNGMIIPSMYNNLGLFINHYP
        210        220        230        240        250
NGVVTVNCAR IIHGNQIATNGVVHVIDRVLTQIGTSIQDFIEAEDDLSSF
        260        270        280        290        300
RAAAITSDIL EALGRDGHFTLFAPTNEAFEKLPRGVLERIMGDKVASEAL
        310        320        330        340        350
MKYHILNTLQ CSESIMGGAVFETLEGNTIEIGCDGDSITVNGIKMVNKKD
        360        370        380        390        400
IVTNNGVIHL IDQVLIPDSAKQVIELAGKQQTTFTDLVAQLGLASALRPD
        410        420        430        440        450
GEYTLLAPVN NAFSDDTLSMDQRLLKLILQNHILKVKVGLNELYNGQILE
        460        470        480        490        500
TIGGKQLRVF VYRTAVCIENSCMEKGSKQGRNGAIHIFREIIKPAEKSLH
        510        520        530        540        550
EKLKQDKRFS TFLSLLEAADLKELLTQPGDWTLFVPTNDAFKGMTSEEKE
        560        570        580        590        600
ILIRDKNALQ NIILYHLTPGVFIGKGFEPGVTNILKTTQGSKIFLKEVND
        610        620        630        640        650
TLLVNELKSK ESDIMTTNGVIHVVDKLLYPADTPVGNDQLLEILNKLIKY
        660        670        680        690        700
IQIKFVRGST FKEIPVTVYKPIIKKYTKIIDGVPVEITEKETREERIITG
        710        720        730        740        750
PEIKYTRIST GGGETEETLKKLLQEDTPVRKLQANKKVQGSRRRLREGRS
Q
```

SEQ ID NO: 5 Human Periostin Isoform 5
(Uniprot Identifier: Q15063-5)

```
        10         20         30         40         50
MIPFLPMFSL LLLLIVNPINANNHYDKILAHSRIRGRDQGPNVCALQQIL
        60         70         80         90         100
GTKKKYFSTC KNWYKKSICGQKTTVLYECCPGYMRMEGMKGCPAVLPIDH
        110        120        130        140        150
VYGTLGIVGA TTTQRYSDASKLREEIEGKGSFTYFAPSNEAWDNLDSDIR
        160        170        180        190        200
RGLESNVNVE LLNALHSHMINKRMLTKDLKNGMIIPSMYNNLGLFINHYP
        210        220        230        240        250
NGVVTVNCAR IIHGNQIATNGVVHVIDRVLTQIGTSIQDFIEAEDDLSSF
        260        270        280        290        300
RAAAITSDIL EALGRDGHFTLFAPTNEAFEKLPRGVLERIMGDKVASEAL
        310        320        330        340        350
MKYHILNTLQ CSESIMGGAVFETLEGNTIEIGCDGDSITVNGIKMVNKKD
        360        370        380        390        400
IVTNNGVIHL IDQVLIPDSAKQVIELAGKQQTTFTDLVAQLGLASALRPD
```

SEQ ID NO: 5 Human Periostin Isoform 5 (Uniprot Identifier: Q15063-5)

```
        410        420        430        440        450
GEYTLLAPVN NAFSDDTLSMDQRLLKLILQNHILKVKVGLNELYNGQILE 460        470        480        490        500
TIGGKQLRVF VYRTAVCIENSCMEKGSKQGRNGAIHIFREIIKPAEKSLH 510        520        530        540        550
EKLKQDKRFS TELSLLEAADLKELLTQPGDWTLFVPTNDAFKGMTSEEKE 560        570        580        590        600
ILIRDKNALQ NIILYHLTPGVFIGKGFEPGVTNILKTTQGSKIFLKEVND 610        620        630        640        650
TLLVNELKSK ESDIMTTNGVIHVVDKLLYPADTPVGNDQLLEILNKLIKY 660        670        680        690        700
IQIKFVRGST FKEIPVTVYRPTLTKVKIEGEPEFRLIKEGETITEVIHGE 710        720        730        740        750
PIIKKYTKII DGVPVEITEKETREERIITGPEIKYTRISTGGGETEETLK 760        770        780        790        800
KLLQEEVTKV TKFIEGGDGHLFEDEEIKRLLQGDTPVRKLQANKKVQGSR

RRLREGRSQ
```

SEQ ID NO: 6 Human Periostin Isoform 6 (Uniprot Identifier: Q15063-6)

```
10         20         30         40         50
MIPFLPMFSL LLLLIVNPINANNHYDKILAHSRIRGRDQGPNVCALQQIL 60         70         80         90         100
GTKKKYFSTC KNWYKKSICGQKTTVLYECCPGYMRMEGMKGCPAVLPIDH 110        120        130        140        150
VYGTLGIVGA TTTQRYSDASKLREEIEGKGSFTYFAPSNEAWDNLDSDIR 160        170        180        190        200
RGLESNVNVE LLNALHSHMINKRMLTKDLKNGMIIPSMYNNLGLFINHYP 210        220        230        240        250
NGVVTVNCAR IIHGNQIATNGVVHVIDRVLTQIGTSIQDFIEAEDDLSSF 260        270        280        290        300
RAAAITSDIL EALGRDGHFTLFAPTNEAFEKLPRGVLERIMGDKVASEAL 310        320        330        340        350
MKYHILNTLQ CSESIMGGAVFETLEGNTIEIGCDGDSITVNGIKMVNKKD 360        370        380        390        400
IVTNNGVIHL IDQVLIPDSAKQVIELAGKQQTTFTDLVAQLGLASALRPD 410        420        430        440        450
GEYTLLAPVN NAFSDDTLSMDQRLLKLILQNHILKVKVGLNELYNGQILE 460        470        480        490        500
TIGGKQLRVF VYRTAVCIENSCMEKGSKQGRNGAIHIFREIIKPAEKSLH 510        520        530        540        550
EKLKQDKRFS TFLSLLEAADLKELLTQPGDWTLFVPTNDAFKGMTSEEKE 560        570        580        590        600
ILIRDKNALQ NIILYHLTPGVFIGKGFEPGVTNILKTTQGSKIFLKEVND 610        620        630        640        650
TLLVNELKSK ESDIMTTNGVIHVVDKLLYPADTPVGNDQLLEILNKLIKY
```

SEQ ID NO: 6 Human Periostin Isoform 6 (Uniprot Identifier: Q15063-6)

```
        660        670        680        690        700
IQIKFVRGST FKEIPVTVYSPEIKYTRISTGGGETEETLKKLLQEEVTKV 710        720        730        740
TKFIEGGDGH LFEDEEIKRLLQGDTPVRKLQANKKVQGSRRRLREGRSQ
```

SEQ ID NO: 7 Human Periostin Isoform 7 (Uniprot Identifier: Q15063-7)

```
10         20         30         40         50
MIPFLPMFSLLLLLLIVNPIN ANNHYDKILAHSRIRGRDQGPNVCALQQIL 60         70         80         90         100
GTKKKYFSTCKNWYKKSICG QKTTVLYECCPGYMRMEGMKGCPAVLPIDH 110        120        130        140        150
VYGTLGIVGATTTQRYSDAS KLREEIEGKGSFTYFAPSNEAWDNLDSDIR 160        170        180        190        200
RGLESNVNVELLNALHSHMI NKRMLTKDLKNGMIIPSMYNNLGLFINHYP 210        220        230        240        250
NGVVTVNCARIIHGNQIATN GVVHVIDRVLTQIGTSIQDFIEAEDDLSSF 260        270        280        290        300
RAAAITSDILEALGRDGHFT LFAPTNEAFEKLPRGVLERIMGDKVASEAL 310        320        330        340        350
MKYHILNTLQCSESIMGGAV FETLEGNTIEIGCDGDSITVNGIKMVNKKD 360        370        380        390        400
IVTNNGVIHLIDQVLIPDSA KQVIELAGKQQTTFTDLVAQLGLASALRPD 410        420        430        440        450
GEYTLLAPVNNAFSDDTLSM DQRLLKLILQNHILKVKVGLNELYNGQILE 460        470        480        490        500
TIGGKQLRVFVYRTAVCIEN SCMEKGSKQGRNGAIHIFREIIKPAEKSLH 510        520        530        540        550
EKLKQDKRFSTELSLLEAAD LKELLTQPGDWTLFVPTNDAFKGMTSEEKE 560        570        580        590        600
ILIRDKNALQNIILYHLTPG VFIGKGFEPGVTNILKTTQGSKIFLKEVND 610        620        630        640        650
TLLVNELKSKESDIMTINGV IHVVDKLLYPADTPVGNDQLLEILNKLIKY 660        670        680        690        700
IQIKFVRGSTFKEIPVTVYS PEIKYTRISTGGGETEETLKKLLQEDTPVR 710        720
KLQANKKVQGSRRRLREGRS Q
```

SEQ ID NO: 8, 9 - Primer sequences

Integrin beta 3 forward primer
SEQ ID NO: 8
atatatatga attcatgcga gcgcagtgg

Integrin beta 3 reverse primer
SEQ ID NO: 9
tatatagaat tottaagtcc cccggtaggt

EXAMPLES

Example 1: Warfarin Compromises Hematopoiesis and HSC Function

In order to test whether warfarin may compromise hematopoiesis via an inhibition of coagulation factors II, VII, IX and X, the inventors treated wildtype mice with warfarin. This led to a modest, but significant increase of the international normalized ratio (INR), a derived measure of the prothrombin time, only at a dose of 0.5 mg/kg (P=0.009) compared to sham-operated control mice. However, when enumerating leukocytes in peripheral blood 14 days after the initiation of treatment, the inventors revealed that the absolute number of leukocytes (P=0.008; FIG. 1A) and monocytes (P=0.007; FIG. 1B) was reduced at the higher dose of warfarin (which prolongs the INR in mice), as well as at the lower dose of warfarin (FIGS. 1A and 1B) which is equivalent to the dose used in humans (approximately 0.05-0.07 mg/kg to achieve an INR between 2-3). The decrease in leukocytes and monocytes appeared as early as three days after initiation of treatment. The percentage of CD11b+ myeloid cells (P=0.003; FIG. 1C) was also decreased. Oral versus subcutaneous administration of warfarin similarly reduced leukocyte and monocyte counts, but subcutaneous treatment was associated with fewer lethal hemorrhagic complications. The lymphocyte count was also decreased, albeit to a lesser extent than myeloid cells. The absolute count and percentage of Lin− c-Kit+ Sca-1+ (LKS), LKS CD150+ CD48− (SLAM) at 2 and 4 weeks and the absolute count and percentage of myeloid progenitor cells in the bone marrow, however, did not significantly differ between controls and warfarin-treated mice. A colony-forming assay revealed that the colony-forming ability of HSPC from warfarin-treated compared to control mice was significantly impaired (P=0.02; FIG. 1D). In response to a one-time dose of 5-fluorouracil-induced 'stress' leukocyte counts were lower in warfarin-treated compared to control mice 7 days after treatment (P=0.03; FIG. 1E) and survival was similarly shortened in mice treated with warfarin at the higher (P=0.0004, long dashes, Log-rank test; FIG. 1F) or the lower dose (P=0.02, dotted line, Log-rank test; FIG. 1F) compared to control mice. Transplantation-based assays to test HSC function in control- versus warfarin-treated mice, revealed impaired function of whole bone marrow cells from a warfarin-treated compared to a control BMM in competitive (P=0.04 after 16 weeks; FIG. 1G), serial (P=0.004 after tertiary transplantation; FIG. 1H) and limiting dilution assays. In fact, the limiting dilution assay revealed a 7.6 fold reduction of functional HSC in warfarin-treated compared to control mice (P=0.0006; FIG. 1I). Colony formation assays of Lin− cells, previously exposed to vehicle or warfarin in vitro for 7 days, in order to rule out a direct toxic effect of warfarin on hematopoietic cells, did not yield significantly different numbers of colonies (FIG. 1J), and culturing of Lin− hematopoietic cells in warfarin-containing media had no direct effect on phenotypical Lin− or LKS cells, the percentage of annexin V+ dead cells, their cycling or myeloid cells. The possibility that warfarin may alter the homing of HSPC in a transplant setting could be excluded, as homing of Lin− and LKS cells to a warfarin-treated BMM was not compromised. In addition, as confirmation of the specificity of the effects of deficient γ carboxylation, administration of vitamin K1 to previously warfarin-treated mice 'rescued' the decreased percentage of myeloid cells (P=0.04). This suggested that the observed detrimental effect of warfarin on hematopoiesis was indeed due to deficient γ carboxylation of vitamin K-dependent factors. Collectively, these results indicate, that warfarin reduces myeloid cells in peripheral blood and impairs the ability of HSPC to adequately respond to hematopoietic 'stress'. This detrimental effect on hematopoiesis seemed to occur indirectly, possibly via detrimental effects on bone marrow stroma.

Example 2: Warfarin Impairs Bone Marrow Stroma

Patients on longterm treatment with warfarin experience bone loss (Rezaieyazdi et al., 2009) and in men taking warfarin the risk of fracture is increased (Gage et al., 2006). In conjunction with our data on the detrimental effects of warfarin on hematopoiesis and previous publications on the support of HSPC by mesenchymal stem cells (MSC) (Mendez-Ferrer et al., 2010) the inventors enumerated Nestin-GFP+ cells, which label MSC, and osteoblastic cells in Nestin-GFP or Col2.3 kb GFP mice, in which the expression of green fluorescent protein (GFP) is driven by the Nestin (Mendez-Ferrer et al., 2010) or Col2.3 kb promoter (Kalajzic et al., 2002), respectively. This revealed a significant reduction of Nestin+ MSC (P=0.047; FIGS. 2A), but no reduction of Col2.3 kb+ osteoblastic cells (FIG. 2B) in mice.

Histomorphometric analysis of distal femora of warfarin-treated mice revealed a significant reduction in cancellous bone mass (FIG. 2C), as shown by a decreased ratio of bone volume/tissue volume (BV/TV P<0.001; FIG. 2D), reduced trabecular number and thickness and increased trabecular separation (FIG. 2C) in warfarin-treated mice compared to control mice. Osteoid volume (OV/BV, P=0.046; FIGS. 2E), osteoblast surface (Ob.S/BS, P=0.0008; FIG. 2F) and osteoclast surface (Oc.S/BS P=0.01) were significantly increased upon treatment with warfarin, as well as the number of osteoblasts (N.Ob/B.Pm, P=0.0001). Osteoclasts were not directly affected by warfarin treatment, as shown by the absence of changes in osteoclast differentiation or number (N.Oc/B.Pm). Taken together these data suggest that warfarin treatment reduces bone formation and osteoblast function (as shown by increased osteoid volume) and increases bone resorption, as shown by the significant increase in osteoclast surface per bone surface.

Hypothesizing that warfarin impairs MSC differentiation, the inventors demonstrated that the differentiation of murine stroma cells to adipocytes and osteoblasts was significantly compromised in presence of warfarin (FIG. 2G). Consistently, the relative expression of osteoblastic genes such as Runt-related transcription factor 2 (Runx2), alkaline phosphatase (Alpl), Col1 (Col1a1), osterix (Osx), osteopontin (Spp1), osteocalcin (Bglap) and others involved in osteoblastic differentiation and function were significantly reduced in primary calvaria cells treated with warfarin compared to vehicle further supporting the hypothesis that warfarin impairs osteoblast function, as suggested by our histomorphometry studies. There was a modest, but significant increase of apoptosis of stroma cells in vitro (P=0.05) after treatment with warfarin.

In order to test the support of HSPC by bone marrow stroma, the inventors performed a cobblestone-formation assay, in which untreated Lin-hematopoietic cells were plated on previously vehicle- or warfarin-treated stroma cells. This revealed a significantly decreased number of cobblestone-forming areas, when the stroma had previously been treated with warfarin (P=0.03; FIG. 2H). Further, coculture of Lin− hematopoietic cells with stroma cells in the presence of warfarin revealed a modest increase of annexin V+ dead hematopoietic cells compared to vehicle treatment (P=0.04). Consistently, in the bone marrow of mice treated with warfarin the inventors observed a modest increase of annexin V+ DAPI+ dead Lin– cells after two weeks (P=0.038) and of annexin V+ DAPI+ dead LKS cells after 6 weeks (P=0.03).

In summary, these data suggest that warfarin reduces the number of MSC, as well as their differentiation capacity to adipocytes and osteoblastic cells. Warfarin impairs osteoblastic function, as well as the HSC-supportive ability of bone marrow stroma cells, leading to compromised function of HSPC.

Example 3: Rebounding of Warfarin-Exposed HSPC in an Untreated Microenvironment

Although a mere reduction of HSC number in warfarin-treated mice did not seem to account for impaired hematopoietic reconstitution upon transplantation (FIG. 1G-I), the inventors assessed whether transplantation of equal numbers of CD45.1+ LKS cells from control or warfarin-treated mice would recapitulate the impaired reconstitution of hematopoietic cells after transplantation of whole bone marrow. Transplantation of equal numbers of CD45.1+ LKS cells from control or warfarin-treated mice into CD45.2+ recipients led to a higher percentage of CD45.1+ donor cells in the peripheral blood of recipients one month (P=0.03), but not two months (P=0.65) after transplantation, if the transplanted bone marrow was derived from warfarin-treated donors. This phenomenon may possibly be due to exhaustion of HSC, which may have entered the cell cycle upon transplantation into an untreated BMM. A higher number of transplanted CD45.1+ LKS cells (and a lower number of competitor cells) achieved higher donor chimerism, but the difference in engraftment between control versus warfarin-treated LKS disappeared and at 16 weeks post transplantation reconstitution by warfarin-treated LKS cells was lower than in the case of control LKS cells, suggesting that functional differences may become more apparent, the greater the 'stress' of transplantation. Further, hypothesizing that an altered cell cycle may account for HSC impairment in a warfarin-versus an untreated BMM, the inventors showed that the percentage of LKS cells in the Go phase of the cell cycle was significantly increased in mice treated with warfarin compared to vehicle (P=0.005). Consistent with a role of pAKT in cell cycling (Liu et al., 2014) the inventors observed a significant reduction of pAKT+ Lin– cells in the bone marrow of warfarin-treated compared to control mice (P=0.04, FIG. 3A). However, transplantation of Lin– cells from a warfarin-treated BMM into an untreated BMM led to an increase of the percentage of Lin– cells in the S/G2/M phases of the cell cycle (P=0.04). Testing the possibility of 'recovery' of warfarin-treated HSPC upon exposure to 'fresh' or untreated stroma as shown in vivo the inventors found an increased number of hematopoietic cells (P=0.009; FIG. 3B) and an increase of the percentage of Lin– cells in the S/G2/M phases of the cell cycle (P=0.02; FIG. 3C), when warfarin-treated Lin– cells were plated on untreated compared to warfarin-treated stroma. Consistently, the number of pAKT+ Lin– cells increased upon plating of previously warfarin-exposed Lin– cells on untreated stroma (P=0.02; FIG. 3D). After adding the AKT-inhibitor MK-2206 to the cocultures, the inventors could confirm that the temporary 'recovery' of warfarin-exposed Lin– cells after plating on untreated stroma was AKT-dependent (P=0.02; FIG. 3E), as treatment with MK-2206 prevented the temporary 'recovery' of hematopoietic cells.

Taken together, this suggested that the detrimental effect of warfarin on HSPC may be due to an induction of a quiescent state via a reduction of pAKT. This may be followed by an increase in cycling status upon replating in vitro or transplantation into an untreated environment via an increase of pAKT, but this effect decreases at later time points, likely due to HSC exhaustion.

Example 4: Warfarin Impairs the HSC-Supportive Function of Bone Marrow Stroma

Hypothesizing that HSC-supportive cytokines may be reduced in a warfarin-treated BMM, the inventors cultured untreated Lin– bone marrow cells in conditioned medium which had been harvested from stroma cells grown in vehicle- or warfarin-containing medium. This revealed a decrease of the total number of hematopoietic cells (P=0.0009; FIG. 3F), as well as a decrease of the myeloid (P=0.001; FIG. 3G) and Lin– cell (P=0.0001; FIG. 3G) fractions in those cultures grown in conditioned medium from warfarin-treated stroma cells. In order to test, which proteins known to support HSC function may be decreased in warfarin-compared to vehicle-treated stroma cells, the inventors performed a focused gene expression analysis. This revealed significant decreases of osteopontin, runt-related transcription factor 2 (Runx 2), as well as chemokine (C-C motif) ligand 3 (Ccl3), angiopoietin (Angpt1), insulin-like growth factor 1 (Igf1), Notch1 and Wnt7b, while stem cell factor (SCF; Kitl) was unchanged and there was a trend towards increased expression of C-X-C motif chemokine 12 (CxCl12). Indeed, granulocyte-colony-stimulating factor (G-CSF)-mediated mobilization of LKS and LKS SLAM cells into peripheral blood was impaired in warfarin-treated mice (P=0.042 and P=0.026, respectively).

In order to test the support of HSPC by stroma directly and in vivo, the inventors intrafemorally cotransplanted vehicle- or warfarin-treated stroma cells with untreated Lin– bone marrow cells. This led to decreased engraftment of total donor bone marrow (P=0.025; FIG. 3H) and donor-derived myeloid cells (P=0.023; FIG. 3I) with persistence and modest expansion of the injected stroma cells at low levels in mice intrafemorally cotransplanted with warfarin-compared to vehicle-treated stroma 14 days after transplantation. Analysis of the identity of the intrafemorally transplanted stroma cells revealed that 60% of these were F4/80+ macrophages at the time of transplantation. Similarly, 14 days after transplantation 80% of the engrafted stroma cells were constituted by F4/80+ macrophages, regardless of whether they had previously been treated with vehicle or warfarin. Macrophages in the bone marrow of primary mice treated with warfarin were not reduced compared to controls. Coculture of untreated Lin– cells on warfarin-treated, sorted F4/80+ macrophages increased the percentage of Annexin V+ apoptotic leukocytes compared to coculture on vehicle-treated macrophages (P=0.034), and protein analysis of sorted F4/80+ macrophages revealed that macrophages are a major source of the vitamin K-dependent protein periostin. However, coimmunoprecipitation of periostin in conditioned medium from vehicle-versus warfarin-treated macrophages and subsequent protein analysis revealed no significant reduction of total periostin levels. Taken together, these in vitro and in vivo data suggest that warfarin-treated stroma is detrimental for hematopoiesis via reduction of functional HSC-supportive proteins leading to a reduction of the reconstitution potential of HSC. This effect may be at least partially mediated by periostin produced by F4/80+ macrophages.

Example 5: Warfarin Impairs Hematopoiesis Via Periostin

Several proteins produced by stromal cells in the BMM, such as osteocalcin, protein Z, Gas 6, matrix gla protein (MGP) and periostin, which is known to be expressed in MSC (Khurana et al., 2016) and osteoblastic cells (Horiuchi et al., 1999; Khurana et al., 2016), require vitamin K for their γ carboxylation (Coutu et al., 2008) and function. Specifically, as a form of posttranslational modification the vitamin-K-dependent enzyme γ glutamylcarboxylase modifies glutamic residues to γ-carboxyglutamic acid (Gla) (Coutu et al., 2008). Therefore, the inventors hypothesized that vitamin K-dependent factors in the BMM and particularly periostin may be responsible for the observed effects on HSPC. Periostin is a secreted extracellular matrix protein, which is expressed by MSC (Coutu et al., 2008; Khurana et al., 2016), osteocytes, periosteal osteoblasts (Bonnet et al., 2012) and bone marrow macrophages, and whose function depends on γ carboxylation. In fact, periostin was shown to be the most abundant Gla-containing protein secreted by MSC (Coutu et al., 2008) and to regulate HSC function (Khurana et al., 2016), while periostin-deficient mice are characterized by anemia, myelomonocytosis and lymphopenia (Khurana et al., 2016). Treatment of periostin knockout mice with warfarin did not lead to a decrease of total leukocytes or monocytes compared to control periostin knockout mice-contrary to wildtype mice treated with warfarin (FIGS. 1A and 1B). In addition, repetitive doses of 75 mg/kg 5-fluorouracil to warfarin-treated periostin knockout mice did not lead to lower leukocyte counts or decreased survival compared to control periostin knockout mice, as previously observed in wildtype mice (FIGS. 1E and 1F). This suggested that periostin and, possibly, the γ-carboxylation of periostin plays a major role in the decrease of myeloid cells after warfarin treatment. Deficiency of other γ-carboxylated proteins in the BMM such as matrix gla protein (El-Maadawy et al., 2003) or osteocalcin (Ducy et al., 1996) to date has not been associated with a hematological phenotype.

In order to test whether the γ-carboxylation of periostin was decreased by warfarin, the inventors performed a coimmunoprecipitation experiment using an anti-gla antibody on conditioned medium from stroma cells treated with vehicle or warfarin (FIG. 3F). Indeed, no γ-carboxylated periostin could be detected in the conditioned medium of warfarin-treated stroma cells (FIG. 4A). Hypothesizing that the lack of (γ-carboxylated) periostin in warfarin-treated mice or in cocultures was the cause of the impairment of hematopoiesis, the inventors added recombinant periostin to cocultures of stroma cells treated with vehicle or warfarin and Lin-bone marrow cells. This restored or 'rescued' the reduced absolute number of hematopoietic cells (P=0.02; FIG. 4B) and led to a strong trend towards restoration of the percentage of LKS cells in warfarin-treated cultures (P=0.056). Additionally, competitive transplantation of total bone marrow from a CD45.1+ donor mouse which had been treated with vehicle or periostin for four days into CD45.2+ recipients led to increased engraftment of CD45.1+ periostin-treated bone marrow four weeks after transplantation (P=0.02; FIG. 4C) but not at later time points (data not shown), suggesting that periostin may augment HSC function short-term. However, treatment of donor mice with vitamin K prior to competitive transplantation did not lead to increased engraftment of donor cells. Competitive transplantation of previously periostin- or vitamin K-treated bone marrow cells also did not lead to an increase in the percentage of LKS cells, an increase in the cell cycle of transplanted LKS cells or an increase in the number of colonies in methylcellulose compared to vehicle. Treatment of mice with periostin and warfarin (or vehicle), however, significantly reduced annexin V+ apoptotic LKS cells compared to mice treated with warfarin (or vehicle) alone (P=0.02; FIG. 4D). Further, in vivo administration of periostin to mice treated with warfarin 'rescued' the percentage of myeloid cells (P=0.007; FIG. 4E).

Example 6: Warfarin Impairs Hematopoiesis Via Periostin/Integrin β3 Signaling Axis In vivo administration of periostin to mice treated with warfarin also 'rescued' the number of LKS cells positive for integrin β3, whose binding to its ligand periostin (Gillan et al., 2002) is known to mediate HSC support (P=0.0013; FIG. 5A) (Khurana and Verfaillie, 2013). The increased percentage of integrin β3+ LKS cells was not due to increased expression of integrin β3+ on LKS cells, as the median fluorescence intensity remained unchanged. An altered physical interaction between periostin and integrin β3 was evident in a coimmunoprecipitation experiment, in which periostin in the conditioned medium of stroma cells exposed to vehicle, but not warfarin (FIG. 4A), efficiently bound integrin β3 overexpressed on 293T cells (FIG. 5B). Quantification showed this to be significant (P=0.02). In order to test, whether the periostin/integrin β3-axis mediates the adhesion of HSPC to stroma, the inventors performed an adhesion assay plating untreated Lin- cells on vehicle- or warfarin-treated stroma cells in the presence or absence of periostin. Indeed, addition of periostin to the cocultures restored or augmented the adhesion of Lin- cells to stroma in warfarin-, but more prominently in vehicle-treated conditions (P=0.03; FIG. 5C). Due to the role of pAKT, which lies downstream of integrin β3 (Hynes, 2002), in periostin-mediated cell survival (Bao et al., 2004) the inventors tested the effect of inhibition of integrin β3 by cilengitide on pAKT in Lin- cells after coculture on BM stroma cells. Similar to the reduction of pAKT+ Lin- cells in mice treated with warfarin (FIG. 3A), inhibition of integrin β3 led to a decrease of pAKT in Lin- cells (P=0.03).

Overall, these data suggest that impairment of HSPC and myeloid cells after warfarin treatment is at least partially mediated by decreased binding of carboxylated periostin to integrin β3 on HSPC leading to decreased support of HSC, likely decreased pAKT signaling and decreased self-renewal of HSC.

Example 7: Vitamin K Antagonism Leads to Reduction of Human Leukocytes and Engraftment of Human HSC Vitamin K antagonists (VKA) are drugs widely used in several conditions in an effort to reduce thromboembolic complications. A possible limitation of its use due to detrimental hematopoietic effects would have extensive consequences. Therefore, in order to test a potential effect of warfarin on human hematopoietic cells, the inventors transplanted untreated human CD34+ cells into vehicle- or warfarin-treated NOD SCID interleukin-2 receptor γ knockout (NSG) mice and demonstrated reduced engraftment of human CD45+ leukocytes in warfarin-compared to vehicle-treated NSG mice (P=0.015; FIG. 6A). Further, intrafemoral cotransplantation of untreated human CD34+ cells with (in vitro) vehicle- or warfarin-treated human stroma cells demonstrated decreased engraftment of human CD45+ leukocytes, when the hematopoietic cells were cotransplanted with warfarin-treated stroma (P=0.046; FIG. 6B), similar to FIGS. 3H and 3I, where this effect seems to have been due to decreased γ-carboxylation of periostin by warfarin-treated macrophages. 6 months after transplantation the transplanted human CD45+ cells were detectable at low levels in the injected and the contralateral femora, but only trends towards lower huCD45+ engraftment in recipients of warfarin-treated stroma were observed. Consistently, although still in the normal reference range, the absolute number of leukocytes (P=0.0007; FIG. 6C) and monocytes (P=0.004; FIG. 6D) and the percentage of basophils (P=0.007; FIG. 6E) and eosinophils (P=0.0027; FIG. 6F) in 282 patients on warfarin, but without hematologic disease, were significantly decreased compared to 145 control patients. Similarly, the absolute number of leukocytes (P=0.029; FIG. 6G) and monocytes (P=0.046; FIG. 6H) was also reduced in 89 patients on fluindione, another VKA, compared to controls. Platelets were not reduced in warfarin- or fluindione-treated patients.

Example 8: VKA Use is More Frequent in People with Versus without a Diagnosis of MDS We hypothesized that the use of VKA may be associated with an increased risk of myelodysplastic syndrome (MDS), a clonal hematopoietic stem cell disorder, which—in mice—may also arise due to impairment of the BMM (Raajimakers et al., 2010; Zambetti et al., 2016).

In a population of men and women aged between 70 and 79 years in 2015 (n=5,464,258) VKA use was more frequent in people with versus without a diagnosis of MDS, both overall (14.66% versus 5.76%, P<0.001; FIG. 7A) and in the various age and sex strata (P<0.001; FIG. 7A). The odds of VKA use was significantly higher in patients with versus without a diagnosis of MDS (adjusted odds ratio: 2.49; 95% confidence interval: 2.31-2.68). As somatic mutations associated with clonal hematopoiesis and the risk of MDS increase with age (Jaiswal et al., 2014) and VKA use may trigger the development of these mutations or MDS risk, the inventors investigated VKA use in patients aged 50-60 (n=11,452, 848). This revealed that VKA use was also more frequent in 50-60 year old patients with versus without a diagnosis of MDS (7.1% versus 0.85%, P<0.001; FIG. 7B). The odds of VKA use in this age group was significantly higher in patients with versus without a diagnosis of MDS and higher than in patients aged 70-79 years (adjusted odds ratio: 8.2; 95% confidence interval: 6.64-10.13). Performance of a myeloid sequencing panel in 5 control and 4 patients on VKA, however, did not reveal any mutations associated with clonal hematopoiesis.

In summary, these data confirm the inventor's data in mice and suggest that treatment with two different vitamin K antagonists reduces the frequency of certain human leukocyte populations, albeit within the normal reference range, and impairs human HSC. Further, the odds of VKA use is increased in patients with MDS.

Example 9: Periostin in Haematological Malignancies

In order to test if periostin may play a role in haematological malignancies, the inventors cocultured K562 or Baf3 p210 cells, both of which are positive for the oncogene BCR-ABL1, which is found in chronic myeloid leukaemia (CML) and B-cell acute lymphoblastic leukaemia (B-ALL), on wildtype versus periostin-deficient bone marrow stromal cells. This revealed increased proliferation of the leukaemic cells when co-cultured on periostin-deficient compared to wildtype bone marrow stromal cells (FIGS. 8A-B). To further check if periostin deficiency has an effect on the progression of leukaemia in vivo, the inventors induced CML in wildtype versus periostin deficient mice via the transplantation of wildtype bone marrow cells transduced with retrovirus expressing the BCR-ABL1 oncogene. It was observed that periostin deficiency in recipient mice accelerated disease progression, as tested by the increased percentage of leukaemic cells (GFP+ (BCR-ABL1+) CD11b+) in peripheral blood (FIG. 8C). Conversely, this suggested that administration of periostin may decrease the progression of myeloid leukaemias.

Methods

Mice 7 to 10 week old C57BL6/N (CD45.2) or SJL (CD45.1; B6.SJL-Ptprca Pepcb/BoyJ), Col1a1 2.3 kb-GFP (kind gift from D. Rowe), Nestin-GFP (Mignone et al., 2004) and periostin knockout mice (kind gift from Juerg Huelsken) were used for these experiments. NOD SCID interleukin (IL)-2 receptor γ deficient (NSG) mice were purchased from Charles River Laboratories (Sulzfeld, Germany) and bred in our facility. All animal studies were approved by the local German government (Regierungspräsidium Darmstadt) in Hessen, Germany, and by the Institutional Animal Care and Use Committee (IACUC) of Boston University.

In Vivo and In Vitro Drug Treatment 0.5 mg/kg/d or 0.05 mg/kg/d of warfarin, resuspended in phosphate-buffered saline was administered to mice via subcutaneously implanted osmotic minipumps (ALZET minipumps, Cupertino, CA). The osmotic minipumps were changed after 14 days (if the experiment went beyond 14 days of treatment). Sham operated (skin incision and suture) mice served as controls. Warfarin treatment continued for 10-14 days. In the xenotransplantation experiments the mice were treated with warfarin via the drinking water (or normal drinking water) at a dose of 0.72 mg/100 ml for a total of 3 days a week (Pfeilschifter et al., 2011).

In the mobilization experiments vehicle- or warfarin-treated C57/B16 mice were treated with 200 μg/kg G-CSF daily for 4 days, sacrificed on day 5 and peripheral blood analyzed for LKS and LKS SLAM cells by flow cytometry.

5-fluorouracil was intraperitoneally injected every week at a dose of 75 mg/kg for a total of 4 doses or as a one time dose of 200 mg/kg. Recombinant mouse periostin (R&D Systems, Minneapolis, MN, cat. no. 2955-F2), produced in the Sf21 (baculovirus)-derived insect cell line, was administered intravenously at a dose of 2-4 μg per day and vitamin K was given at a dose of 15 mg/kg by oral gavage for four consecutive days.

Concentrations of drugs for in vitro use were 2 μM for warfarin, 2 μg/ml for periostin, 5 μM for the AKT inhibitor MK-2206 (Selleck Chemicals, Houston, TX) and cilengitide (Selleck Chemicals, Houston, TX, Cat. No. #S7077) was used at 0.05 μM. Phosphate buffered saline served as the vehicle control.

Bone Marrow Transplantation and In Vivo Assays

SJL (CD45.1) donor mice were treated with vehicle or warfarin, euthanized and long bones were flushed, followed by RBC lysis (Life Technologies, Darmstadt, Germany). For competitive transplantation $2 \times 10^6$ total BM cells from SJL mice were co-transplanted with $1 \times 10^6$ CD45.2+ BM competitor cells into lethally irradiated (900 cGy) C57BL/6N (CD45.2+) recipient mice. For serial transplantation $2 \times 10^6$ total CD45.1+ BM cells were transplanted into lethally irradiated C57BL/6N recipient mice. Cell engraftment and chimerism were assessed by flow cytometry of peripheral blood leukocytes for CD45.1 and CD45.2 after 4, 8, 12 and 16 weeks post transplantation. In the limiting dilution experiment we treated primary CD45.1+ donor mice with vehicle or warfarin for 14 days and, consequently, transplanted $5\times10^5$, $12.5\times10^4$, $6\times10^4$ and $1.5\times10^4$ pooled BM cells into 5 CD45.2+ recipients per group adding $5\times10^5$ CD45.2+ supporter cells. In indicated experiments we transplanted 5,000 or 10,000 sorted CD45.1+ LKS cells from mice treated with vehicle or warfarin plus $1\times10^6$ CD45.2+ total BM supporter cells into CD45.2+ recipient mice.

In the homing assay, we intravenously transplanted $9\times10^6$ Actin DsRed+ whole BM cells into C57BL/6N mice treated with vehicle or warfarin for 14 days. 18 hours later, we analyzed BM and spleen cells of recipient mice for the presence of DsRed+ LKS cells.

For the xenotransplantation experiments, we intravenously injected $1.3\times10^5$ human CD34+ cells, obtained via magnetic separation by magnetic beads (Miltenyi Biotech, Bergisch Gladbach, Germany) from BM filters used after harvest of non-mobilized HSPC from healthy allogeneic donors, into irradiated (250 cGy) NSG mice, which had previously been treated with vehicle or warfarin for 14 days.

For the intrafemoral co-transplantation experiments $0.8\times10^5$ human CD34+ cells or $1\times10^5$ Lin– cells from Actin-DsRed reporter mice were mixed with $5\times10^5$ human or murine stroma cells which had been expanded in vitro and pretreated with vehicle or 2 µM warfarin for 14 days. The human stromal cells had been obtained via flushing of discarded bones from the orthopedic operating room, as approved of by the local ethics committee.

Analysis of Mice

We assessed the complete blood count of vehicle or warfarin-treated mice using a complete blood count analyzer (Scil Vet ABC, Gurnee, IL). Peripheral blood and bone marrow samples were stained with antibodies for flow cytometry, which was performed on a BD LSR Fortessa (BD Biosciences, Heidelberg, Germany). The lineage antibody cocktail contained antibodies to B220, CD5, Ter119, F4/80 and CD11b. Engraftment of human cells in NSG mice was assessed using anti-human CD45 (BD Biosciences, San José, CA).

For cell cycle analysis cells were permeabilized and fixed with the cytoperm/cytofix kit (BD Biosciences, San Jose, CA), followed by staining with an antibody to Ki67-PE (Biolegend, San Diego, CA) overnight at 4 C. Consequently, cells were washed and resuspended in PBS with DAPI (1 ng/ml). For detection of apoptosis cells were first stained for surface markers, washed with Annexin V buffer (Life Technologies, Darmstadt, Germany), stained with Annexin V-PE (Life Technologies, Darmstadt, Germany), washed with Annexin V binding buffer, resuspended in PBS with DAPI and analyzed.

The PE-labelled anti-pAKT antibody (Cell signaling, #5315, Danvers, MA) was used for intracellular flow cytometry after fixation and permeabilization of the cells.

Bone Histomorphometry

The femora were isolated and first fixed in 4% paraformaldehyde at 4C overnight and then in 70% ethanol for an additional 5 days. Fixed bones were dehydrated in graded ethanol, then embedded in methyl methacrylate without demineralization. Undecalcified 5 µm thick longitudinal sections were obtained using a microtome (RM2255, Leica Biosystem, IL, USA). The sections were stained with Goldner Trichrome and at least two consecutive sections per specimen were examined for measurements of cellular parameters. A standard histomorphometric analysis of the femur methaphysis was performed using the Osteomeasure analysis system (Osteometrics Inc, Decatur, GA, USA). Measurements were performed 200 µm below the distal growth plate. The observer was blinded to the experimental group at the time of measurement. The cellular parameters were calculated and expressed according to the standardized nomenclature (Dempster et al., 2013).

In Vitro Assays

In the co-culture and cobblestone assays 20,000 Lin– cells were plated on stroma cells, which had been grown and expanded from vehicle- or warfarin-treated mice in medium (α-MEM medium supplemented with 20% fetal bovine serum, 1% penicillin/streptomycin, 1% L-Glutamine) containing vehicle or warfarin (2 µM). Conditioned medium was harvested from stroma from 5 mice grown in the above medium containing vehicle or warfarin for 7 days. Consequently, 100,000 Lin– cells were grown for 2-3 days in the conditioned medium and analyzed for cell counts by flow cytometry. Where indicated, the conditioned medium was concentrated using Microsep Advance Centrifugal Devices 30K Omega (Pall Life Sciences, Portsmouth, UK).

For all coculture assays hematopoietic and stroma cells were derived from the same mouse strain (C57/Bl6). Stroma cells were used after a maximum of two passages and when they were 70-80% confluent. Stroma cells were derived by crushing bones from mice, plating them in α-MEM medium containing 20% fetal calf serum, penicillin/strptomycin and by removing non-adherent hematopoietic cells the following day, as described (Mukherjee et al., 2008).

For the methylcellulose colony assays, we plated 10,000 total BM cells from vehicle- or warfarin-treated mice in methylcellulose (M3434, Stem Cell Technologies, Vancouver, Canada). We scored colonies after 10 days.

To test the direct effect of warfarin on hematopoietic cells 100,000 Lin– cells were cultured in 2 µM vehicle or warfarin in the absence of stroma cells for a total of 7 days. For the in vitro rescue experiment with periostin stroma cells were grown in warfarin for 14 days, before vehicle or periostin were added.

For the macrophage coculture assay F4/80+ macrophages were sorted from the bone marrow of control or warfarin-treated mice, plated and cocultured with 20,000-30,000 Lin– BM cells as from the following day.

Differentiation Assays

Bones from mice were crushed and plated and hematopoietic cells were removed the following day. As described (Mukherjee et al., 2008), after reaching confluence the stroma cells were cultured in α-MEM medium containing 10 mM β-glycerolphosphate, 10 nM dexamethasone and 50 µg/ml ascorbic acid for differentiation into osteoblastic cells (Mukherjee et al., 2008) or 500 nM insulin and 100 nM dexamethasone for differentiation into adipocytes. Differentiation was tested after 14-20 days by staining for von Kossa in the case of osteoblastic cells and Oil Red O in the case of adipocytes following standard staining protocols. Osteoclasts were purified from bone marrow macrophages, following standard protocols. Briefly, bone marrow cells were isolated from the femora and tibiae of 6-8 week old C57/B16 animals and cultured overnight at 37 C in α-MEM medium containing 10% fetal bovine serum and 1% antibiotic/antimycotic. The following day non-adherent cells were collected and separated by centrifugation on 50% Ficoll-Paque. Bone marrow-derived macrophages were seeded at 20,000 cells/well and cultured for 3 days in the presence of macrophage colony-stimulating factor (M-CSF) (50 ng/ml). On day 4 cells were also treated with receptor activator of nuclear factor kappa-B ligand (RANKL) (50 ng/ml) for an additional 4-5 days prior to tartrate-resistant acid phosphatase (TRAP) staining. Cells were treated with vehicle or warfarin (2 μM) for the entire culture period. For TRAP staining cells were fixed in 10% formalin for 10 minutes, permeabilized in acetone:ethanol (50:50) for 1 minute and then stained with TRAP solution (1 mg/ml of naphtol AS-MX in 0.1 M sodium acetate, 0.05M sodium tartrate and 0.6 mg/ml violet blue salt) at 37 C for 10-15 minutes.

Cloning of the Integrin β3 Construct

Integrin β3 was amplified by PCR from 3T3 fibroblasts using the forward and the reverse primers, ATATATAT-GAATTCATGCGAGCGCAGTGG (SEQ ID NO: 8) and TATATAGAATTCITAAGTCCCCCGGTAGGT (SEQ ID NO: 9), respectively. Both primers contained an EcoR1 restriction site, which was used to clone the 2.3 kb integrin β3 fragment into the MSCV IRES GFP vector. Integrin B3 expression was checked by flow cytometry (BD Biosciences, San José, CA) and Western Blotting (Abcam, Cambridge, UK, and Cell Signaling, Danvers, MA, as described (Krause et al., 2013).

Quantitative PCR

Quantitative PCR was performed using standard protocols.

Measurement of the INR

A Coaguchek XS (Roche Diagnostics, Mannheim, Germany) and Coaguchek XS PT test strips were used to determine the INR of vehicle- and warfarin-treated mice.

Western Blotting and Co-Immunoprecipitation

HEK293T cells were transfected with the MSCV integrin β3 IRES GFP plasmid using calcium phosphate transfection. Conditioned medium from vehicle or warfarin-treated stroma cells was added 48 h post transfection for 6 hours followed by protein isolation using RIPA buffer (150 mM sodium chloride, 1.0% Triton X-100, 0.5% sodium deoxycholate, 0.1% SDS, sodium dodecyl sulfate, 50 mM Tris, pH 8.0). Magnetic beads (Dynabeads Protein G) were used for protein immunoprecipitation (IP). Protein lysates were first incubated in 2 μg of antibody for 3 h at 4 C and then incubated with magnetic beads overnight at 4 C. After washing three times in ice cold lysis buffer immunoprecipitated proteins were mixed with 5× Laemmli elution buffer, heated to 95 C for 4 min and eluted. Proteins were separated using SDS-PAGE (4-12% gradient) and blotted onto nitrocellulose membranes. Membranes were incubated overnight in the respective primary antibodies at 4 C and then in secondary antibodies for 1 h at room temperature.

For the anti-gla coimmunoprecipitation experiments we used 4 μg of anti-Gla antibody (BioMedica Diagnostics Inc., Windsor, Canada). In the periostin-overexpression experiments HEK293T cells were transfected with a Myc-DDK-tagged periostin-expressing plasmid (Origene #MR210633). 12 hours after transfection, the media was changed to fresh media containing warfarin (2 μM and 50 μM) or vitamin K1 (10 μg/ml) and left for 48 hours. Cell lysates were then prepared using RIPA lysis buffer.

Isolation of Human CD34+ and Stroma Cells and Patient Data

Stroma and hematopoietic cells (purified for CD34+) were taken from the iliac crest of healthy donors of allogeneic bone marrow.

For FIGS. 6C-6H: Data of patients on VKA were obtained from the French health care databases. Patients with hematological disease, inflammation or sepsis were excluded. Patients admitted to the hospital for dermatological problems without hematological disease or sepsis acted as controls. The control patients did not have clots and were not treated with VKA or any other anticoagulant.

Sequencing of Patients

Sequencing of 50 to 60 year old patients on warfarin or control patients was performed using the TrueSight Myeloid Sequencing Panel (Illumina, San Diego, CA).

The control group was composed of patients with no past history of clots, no VKA treatment and no genetic predisposition to thrombosis, while the study group consisted of patients with long-term VKA treatment for thrombosis. None of these patients had a known hematological disorder.

Epidemiological Study

The national healthcare administrative databases in France were used to explore a potential association between VKA use and a diagnosis of MDS. The French National Health Insurance Information System (SNIIRAM) collects all individualized and anonymous healthcare claims including drug usage and severe and long-term conditions listed in the International Classification of Diseases, $10^{th}$ edition (ICD-10). Information from the SNIIRAM database was cross-referenced with the French hospital discharge database (PMSI), which provides discharge diagnoses (ICD-10 codes) for all patients.

The study population consisted of French men and women aged 70-79 years (n=5,464,258) or 50-60 years (n=11,452,848) in 2015. Individuals were considered VKA users if they had at least one VKA claim in 2015, and MDS diagnosis was identified from ICD-10 codes (D46) allocated to hospital stays and/or long-term illness diagnosis in 2015 (n=5,840 cases). In France, fluindione, warfarin and acenocoumarol are available as VKA.

Statistical Methods

Chi-squared test and logistic regression adjusted for age and sex were used to compare the odds of VKA use in individuals with versus without a diagnosis of MDS, overall and by age and sex strata.

Differences in survival were assessed by Kaplan-Meier non-parametric estimates (Log-rank test) and between groups by student's t-test. The data were presented as mean±s.d. We used L-Calc software (Stemcell Technologies, Vancouver, Canada) to calculate HSC frequency by Poisson statistics. P values≤0.05 were accepted as significant.

The invention claimed is:

1. An in-vitro method for preparing a stem cell transplant with improved transplantation success, the method comprising:
   a. providing a composition of stem cells,
   b. contacting the composition of stem cells with a periostin compound, wherein the periostin compound is selected from a periostin protein, or a functional fragment or variant thereof, or a periostin nucleic acid encoding the periostin protein, or encoding the functional fragment or variant thereof,
   c. incubating the mixture of b for a sufficient amount of time to obtain a suitable stem cell transplant.

2. The method according to claim 1, wherein the stem cells are HSC derived from an umbilical cord blood sample or from a bone marrow sample.

3. The method according to claim 1, wherein the method further comprises culturing and/or purifying the stem cell transplant.

4. The method according to claim 1, wherein the stem cells are HSC.

* * * * *

SEQUENCE LISTING

<160> NUMBER OF SEQ ID NOS: 9

<210> SEQ ID NO 1
<211> LENGTH: 836
<212> TYPE: PRT
<213> ORGANISM: Homo sapiens

<400> SEQUENCE: 1

```
Met Ile Pro Phe Leu Pro Met Phe Ser Leu Leu Leu Leu Ile Val
1               5               10              15

Asn Pro Ile Asn Ala Asn Asn His Tyr Asp Lys Ile Leu Ala His Ser
        20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
        210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
            245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
            325                 330                 335

Ser Ile Thr Val Asn Gly Ile Lys Met Val Asn Lys Asp Ile Val
        340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
```

```
                420             425             430
Ile Leu Lys Val Lys Val Gly Leu Asn Glu Leu Tyr Asn Gly Gln Ile
            435             440             445

Leu Glu Thr Ile Gly Gly Lys Gln Leu Arg Val Phe Val Tyr Arg Thr
450             455             460

Ala Val Cys Ile Glu Asn Ser Cys Met Glu Lys Gly Ser Lys Gln Gly
465             470             475             480

Arg Asn Gly Ala Ile His Ile Phe Arg Glu Ile Ile Lys Pro Ala Glu
            485             490             495

Lys Ser Leu His Glu Lys Leu Lys Gln Asp Lys Arg Phe Ser Thr Phe
            500             505             510

Leu Ser Leu Leu Glu Ala Ala Asp Leu Lys Glu Leu Leu Thr Gln Pro
            515             520             525

Gly Asp Trp Thr Leu Phe Val Pro Thr Asn Asp Ala Phe Lys Gly Met
            530             535             540

Thr Ser Glu Glu Lys Glu Ile Leu Ile Arg Asp Lys Asn Ala Leu Gln
545             550             555             560

Asn Ile Ile Leu Tyr His Leu Thr Pro Gly Val Phe Ile Gly Lys Gly
            565             570             575

Phe Glu Pro Gly Val Thr Asn Ile Leu Lys Thr Thr Gln Gly Ser Lys
            580             585             590

Ile Phe Leu Lys Glu Val Asn Asp Thr Leu Leu Val Asn Glu Leu Lys
            595             600             605

Ser Lys Glu Ser Asp Ile Met Thr Thr Asn Gly Val Ile His Val Val
            610             615             620

Asp Lys Leu Leu Tyr Pro Ala Asp Thr Pro Val Gly Asn Asp Gln Leu
625             630             635             640

Leu Glu Ile Leu Asn Lys Leu Ile Lys Tyr Ile Gln Ile Lys Phe Val
            645             650             655

Arg Gly Ser Thr Phe Lys Glu Ile Pro Val Thr Val Tyr Thr Thr Lys
            660             665             670

Ile Ile Thr Lys Val Val Glu Pro Lys Ile Lys Val Ile Glu Gly Ser
            675             680             685

Leu Gln Pro Ile Ile Lys Thr Glu Gly Pro Thr Leu Thr Lys Val Lys
            690             695             700

Ile Glu Gly Glu Pro Glu Phe Arg Leu Ile Lys Glu Gly Glu Thr Ile
705             710             715             720

Thr Glu Val Ile His Gly Glu Pro Ile Ile Lys Lys Tyr Thr Lys Ile
            725             730             735

Ile Asp Gly Val Pro Val Glu Ile Thr Glu Lys Glu Thr Arg Glu Glu
            740             745             750

Arg Ile Ile Thr Gly Pro Glu Ile Lys Tyr Thr Arg Ile Ser Thr Gly
            755             760             765

Gly Gly Glu Thr Glu Glu Thr Leu Lys Lys Leu Leu Gln Glu Glu Val
            770             775             780

Thr Lys Val Thr Lys Phe Ile Glu Gly Gly Asp Gly His Leu Phe Glu
785             790             795             800

Asp Glu Glu Ile Lys Arg Leu Leu Gln Gly Asp Thr Pro Val Arg Lys
            805             810             815

Leu Gln Ala Asn Lys Lys Val Gln Gly Ser Arg Arg Leu Arg Glu
            820             825             830

Gly Arg Ser Gln
            835
```

<210> SEQ ID NO 2
<211> LENGTH: 779
<212> TYPE: PRT
<213> ORGANISM: Homo sapiens

<400> SEQUENCE: 2

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
```

```
            370                 375                 380
Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
                610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
                660                 665                 670

Ile Lys Lys Tyr Thr Lys Ile Ile Asp Gly Val Pro Val Glu Ile Thr
                675                 680                 685

Glu Lys Glu Thr Arg Glu Glu Arg Ile Ile Thr Gly Pro Glu Ile Lys
                690                 695                 700

Tyr Thr Arg Ile Ser Thr Gly Gly Glu Thr Glu Thr Leu Lys
705                 710                 715                 720

Lys Leu Leu Gln Glu Glu Val Thr Lys Val Thr Lys Phe Ile Glu Gly
                725                 730                 735

Gly Asp Gly His Leu Phe Glu Asp Glu Ile Lys Arg Leu Leu Gln
                740                 745                 750

Gly Asp Thr Pro Val Arg Lys Leu Gln Ala Asn Lys Lys Val Gln Gly
                755                 760                 765

Ser Arg Arg Arg Leu Arg Glu Gly Arg Ser Gln
770                 775

<210> SEQ ID NO 3
```

```
<211> LENGTH: 781
<212> TYPE: PRT
<213> ORGANISM: Homo sapiens

<400> SEQUENCE: 3

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
                340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
```

```
                385                 390                 395                 400
        Gly Glu Tyr Thr Leu Leu Ala Pro Val Asn Asn Ala Phe Ser Asp Asp
                        405                 410                 415

Thr Leu Ser Met Asp Gln Arg Leu Leu Lys Leu Ile Leu Gln Asn His
                        420                 425                 430

Ile Leu Lys Val Lys Val Gly Leu Asn Glu Leu Tyr Asn Gly Gln Ile
                        435                 440                 445

Leu Glu Thr Ile Gly Gly Lys Gln Leu Arg Val Phe Val Tyr Arg Thr
                450                 455                 460

Ala Val Cys Ile Glu Asn Ser Cys Met Glu Lys Gly Ser Lys Gln Gly
        465                 470                 475                 480

Arg Asn Gly Ala Ile His Ile Phe Arg Glu Ile Ile Lys Pro Ala Glu
                        485                 490                 495

Lys Ser Leu His Glu Lys Leu Lys Gln Asp Lys Arg Phe Ser Thr Phe
                        500                 505                 510

Leu Ser Leu Leu Glu Ala Ala Asp Leu Lys Glu Leu Leu Thr Gln Pro
                        515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
        545                 550                 555                 560

Asn Ile Ile Leu Tyr His Leu Thr Pro Gly Val Phe Ile Gly Lys Gly
                        565                 570                 575

Phe Glu Pro Gly Val Thr Asn Ile Leu Lys Thr Thr Gln Gly Ser Lys
                        580                 585                 590

Ile Phe Leu Lys Glu Val Asn Asp Thr Leu Leu Val Asn Glu Leu Lys
                        595                 600                 605

Ser Lys Glu Ser Asp Ile Met Thr Thr Asn Gly Val Ile His Val Val
                610                 615                 620

Asp Lys Leu Leu Tyr Pro Ala Asp Thr Pro Val Gly Asn Asp Gln Leu
        625                 630                 635                 640

Leu Glu Ile Leu Asn Lys Leu Ile Lys Tyr Ile Gln Ile Lys Phe Val
                        645                 650                 655

Arg Gly Ser Thr Phe Lys Glu Ile Pro Val Thr Val Tyr Arg Pro Thr
                        660                 665                 670

Leu Thr Lys Val Lys Ile Glu Gly Glu Pro Glu Phe Arg Leu Ile Lys
                        675                 680                 685

Glu Gly Glu Thr Ile Thr Glu Val Ile His Gly Glu Pro Ile Ile Lys
                690                 695                 700

Lys Tyr Thr Lys Ile Ile Asp Gly Val Pro Val Glu Ile Thr Glu Lys
        705                 710                 715                 720

Glu Thr Arg Glu Glu Arg Ile Ile Thr Gly Pro Glu Ile Lys Tyr Thr
                        725                 730                 735

Arg Ile Ser Thr Gly Gly Gly Glu Thr Glu Thr Leu Lys Lys Leu
                        740                 745                 750

Leu Gln Glu Asp Thr Pro Val Arg Lys Leu Gln Ala Asn Lys Lys Val
                        755                 760                 765

Gln Gly Ser Arg Arg Leu Arg Glu Gly Arg Ser Gln
                770                 775                 780

<210> SEQ ID NO 4
<211> LENGTH: 751
<212> TYPE: PRT
<213> ORGANISM: Homo sapiens
```

<400> SEQUENCE: 4

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65              70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
```

```
                    405                 410                 415
Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Gly Glu Thr Glu Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Arg Leu Arg Glu Gly Arg Ser Gln
            740                 745                 750

<210> SEQ ID NO 5
<211> LENGTH: 809
<212> TYPE: PRT
<213> ORGANISM: Homo sapiens

<400> SEQUENCE: 5

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30
```

```
Arg Ile Arg Gly Arg Asp Gln Gly Pro Asn Val Cys Ala Leu Gln Gln
         35                  40                  45

Ile Leu Gly Thr Lys Lys Tyr Phe Ser Thr Cys Lys Asn Trp Tyr
 50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
             100                 105                 110

Thr Gln Arg Tyr Ser Asp Ala Ser Lys Leu Arg Glu Glu Ile Glu Gly
         115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                 165                 170                 175

Lys Asp Leu Lys Asn Gly Met Ile Ile Pro Ser Met Tyr Asn Asn Leu
             180                 185                 190

Gly Leu Phe Ile Asn His Tyr Pro Asn Gly Val Val Thr Val Asn Cys
         195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                 245                 250                 255

Ser Asp Ile Leu Glu Ala Leu Gly Arg Asp Gly His Phe Thr Leu Phe
             260                 265                 270

Ala Pro Thr Asn Glu Ala Phe Glu Lys Leu Pro Arg Gly Val Leu Glu
         275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                 325                 330                 335

Ser Ile Thr Val Asn Gly Ile Lys Met Val Asn Lys Lys Asp Ile Val
             340                 345                 350

Thr Asn Asn Gly Val Ile His Leu Ile Asp Gln Val Leu Ile Pro Asp
         355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                 405                 410                 415

Thr Leu Ser Met Asp Gln Arg Leu Leu Lys Leu Ile Leu Gln Asn His
             420                 425                 430

Ile Leu Lys Val Lys Val Gly Leu Asn Glu Leu Tyr Asn Gly Gln Ile
         435                 440                 445

Leu Glu Thr Ile Gly Gly Lys Gln Leu Arg Val Phe Val Tyr Arg Thr
```

```
                    450                 455                 460
Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                    485                 490                 495

Lys Ser Leu His Glu Lys Leu Lys Gln Asp Lys Arg Phe Ser Thr Phe
                    500                 505                 510

Leu Ser Leu Leu Glu Ala Ala Asp Leu Lys Glu Leu Leu Thr Gln Pro
515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                    565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                    645                 650                 655

Arg Gly Ser Thr Phe Lys Glu Ile Pro Val Thr Val Tyr Arg Pro Thr
                660                 665                 670

Leu Thr Lys Val Lys Ile Glu Gly Glu Pro Glu Phe Arg Leu Ile Lys
            675                 680                 685

Glu Gly Glu Thr Ile Thr Glu Val Ile His Gly Glu Pro Ile Ile Lys
690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                    725                 730                 735

Arg Ile Ser Thr Gly Gly Gly Thr Glu Glu Thr Leu Lys Lys Leu
                740                 745                 750

Leu Gln Glu Glu Val Thr Lys Val Thr Lys Phe Ile Glu Gly Gly Asp
            755                 760                 765

Gly His Leu Phe Glu Asp Glu Ile Lys Arg Leu Leu Gln Gly Asp
770                 775                 780

Thr Pro Val Arg Lys Leu Gln Ala Asn Lys Lys Val Gln Gly Ser Arg
785                 790                 795                 800

Arg Arg Leu Arg Glu Gly Arg Ser Gln
                805

<210> SEQ ID NO 6
<211> LENGTH: 749
<212> TYPE: PRT
<213> ORGANISM: Homo sapiens

<400> SEQUENCE: 6

Met Ile Pro Phe Leu Pro Met Phe Ser Leu Leu Leu Leu Leu Ile Val
1               5                   10                  15
```

-continued

```
Asn Pro Ile Asn Ala Asn His Tyr Asp Lys Ile Leu Ala His Ser
             20                  25                  30

Arg Ile Arg Gly Arg Asp Gln Gly Pro Asn Val Cys Ala Leu Gln Gln
         35                  40                  45

Ile Leu Gly Thr Lys Lys Lys Tyr Phe Ser Thr Cys Lys Asn Trp Tyr
     50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
```

```
                    435                 440                 445
Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Ser Pro Glu
                660                 665                 670

Ile Lys Tyr Thr Arg Ile Ser Thr Gly Gly Gly Glu Thr Glu Glu Thr
                675                 680                 685

Leu Lys Lys Leu Leu Gln Glu Glu Val Thr Leu Val Thr Lys Phe Ile
                690                 695                 700

Glu Gly Gly Asp Gly His Leu Phe Glu Asp Glu Ile Lys Arg Leu
705                 710                 715                 720

Leu Gln Gly Asp Thr Pro Val Arg Lys Leu Gln Ala Asn Lys Lys Val
                725                 730                 735

Gln Gly Ser Arg Arg Arg Leu Arg Glu Gly Arg Ser Gln
                740                 745

<210> SEQ ID NO 7
<211> LENGTH: 721
<212> TYPE: PRT
<213> ORGANISM: Homo sapiens

<400> SEQUENCE: 7

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
                35                  40                  45

Ile Leu Gly Thr Lys Lys Lys Tyr Phe Ser Thr Cys Lys Asn Trp Tyr
                50                  55                  60
```

```
Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
```

```
                485             490             495
Lys Ser Leu His Glu Lys Leu Lys Gln Asp Lys Arg Phe Ser Thr Phe
            500             505             510
Leu Ser Leu Leu Glu Ala Ala Asp Leu Lys Glu Leu Leu Thr Gln Pro
            515             520             525
Gly Asp Trp Thr Leu Phe Val Pro Thr Asn Asp Ala Phe Lys Gly Met
            530             535             540
Thr Ser Glu Glu Lys Glu Ile Leu Ile Arg Asp Lys Asn Ala Leu Gln
545             550             555             560
Asn Ile Ile Leu Tyr His Leu Thr Pro Gly Val Phe Ile Gly Lys Gly
                565             570             575
Phe Glu Pro Gly Val Thr Asn Ile Leu Lys Thr Thr Gln Gly Ser Lys
            580             585             590
Ile Phe Leu Lys Glu Val Asn Asp Thr Leu Leu Val Asn Glu Leu Lys
            595             600             605
Ser Lys Glu Ser Asp Ile Met Thr Thr Asn Gly Val Ile His Val Val
            610             615             620
Asp Lys Leu Leu Tyr Pro Ala Asp Thr Pro Val Gly Asn Asp Gln Leu
625             630             635             640
Leu Glu Ile Leu Asn Lys Leu Ile Lys Tyr Ile Gln Ile Lys Phe Val
                645             650             655
Arg Gly Ser Thr Phe Lys Glu Ile Pro Val Thr Val Tyr Ser Pro Glu
                660             665             670
Ile Lys Tyr Thr Arg Ile Ser Thr Gly Gly Gly Glu Thr Glu Glu Thr
            675             680             685
Leu Lys Lys Leu Leu Gln Glu Asp Thr Pro Val Arg Lys Leu Gln Ala
            690             695             700
Asn Lys Lys Val Gln Gly Ser Arg Arg Arg Leu Arg Glu Gly Arg Ser
705             710             715             720
Gln

<210> SEQ ID NO 8
<211> LENGTH: 29
<212> TYPE: DNA
<213> ORGANISM: Artificial
<220> FEATURE:
<223> OTHER INFORMATION: Integrin beta 3 forward primer

<400> SEQUENCE: 8
atatatatga attcatgcga gcgcagtgg                               29

<210> SEQ ID NO 9
<211> LENGTH: 30
<212> TYPE: DNA
<213> ORGANISM: Artificial
<220> FEATURE:
<223> OTHER INFORMATION: Integrin beta 3 reverse primer

<400> SEQUENCE: 9
tatatagaat tcttaagtcc cccggtaggt                              30
```